US008754365B2

(12) United States Patent
Krechmer et al.

(10) Patent No.: US 8,754,365 B2
(45) Date of Patent: Jun. 17, 2014

(54) APPARATUS AND METHOD FOR THERMAL ASSISTED DESORPTION IONIZATION SYSTEMS

(71) Applicant: Ionsense Inc., Saugus, MA (US)

(72) Inventors: Jordan Krechmer, Melrose, MA (US); Brian D. Musselman, Melrose, MA (US)

(73) Assignee: Ionsense, Inc., Saugus, MA (US)

( * ) Notice: Subject to any disclaimer, the term of this patent is extended or adjusted under 35 U.S.C. 154(b) by 0 days.

(21) Appl. No.: 13/797,409

(22) Filed: Mar. 12, 2013

(65) Prior Publication Data

US 2013/0280812 A1      Oct. 24, 2013

Related U.S. Application Data

(63) Continuation of application No. 13/364,322, filed on Feb. 2, 2012.

(60) Provisional application No. 61/439,866, filed on Feb. 5, 2011, provisional application No. 61/582,204, filed on Dec. 30, 2011, provisional application No. 61/587,218, filed on Jan. 17, 2012.

(51) Int. Cl.
  *G01N 27/64* (2006.01)
  *H01J 49/04* (2006.01)
  *H01J 49/00* (2006.01)
  *G01N 27/62* (2006.01)

(52) U.S. Cl.
  CPC ............ *H01J 49/004* (2013.01); *G01N 27/622* (2013.01); *G01N 27/64* (2013.01)
  USPC ........ 250/282; 250/281; 250/288; 250/423 R; 250/423 P; 250/424

(58) Field of Classification Search
  CPC ....... H01J 49/004; H01J 49/005; H01J 49/06; H01J 49/063; H01J 49/067; H01J 49/423; H01J 49/427; H01J 49/4265; H01J 49/4225; G01N 27/622; G01N 27/64
  See application file for complete search history.

(56) References Cited

U.S. PATENT DOCUMENTS

| 3,633,027 A | 1/1972 | Ryhage |
| 3,957,470 A | 5/1976 | Dawes |

(Continued)

FOREIGN PATENT DOCUMENTS

| DE | 102007015542 | 10/2007 |
| GB | 2263578 | 7/1993 |

(Continued)

OTHER PUBLICATIONS

Barber, M. et al., "Fast atom bombardment of solids (F.A.B.): a new ion source for mass spectrometry" J.Chem. Soc. Chem. Commun., 1981, 325.

(Continued)

*Primary Examiner* — David A Vanore
(74) *Attorney, Agent, or Firm* — Sci-Law Strategies, P.C.

(57) ABSTRACT

The present invention is directed to a method and device to desorb an analyte using heat to allow desorption of the analyte molecules, where the desorbed analyte molecules are ionized with ambient temperature ionizing species. In various embodiments of the invention a current is passed through a mesh upon which the analyte molecules are present. The current heats the mesh and results in desorption of the analyte molecules which then interact with gas phase metastable neutral molecules or atoms to form analyte ions characteristic of the analyte molecules.

20 Claims, 24 Drawing Sheets

(56) References Cited

U.S. PATENT DOCUMENTS

| | | | |
|---|---|---|---|
| 4,016,421 A | 4/1977 | Hull | |
| 4,144,451 A | 3/1979 | Kambara | |
| 4,213,326 A | 7/1980 | Brodasky | |
| 4,542,293 A | 9/1985 | Fenn | |
| 4,546,253 A | 10/1985 | Tsuchiya | |
| 4,654,052 A | 3/1987 | Sharp | |
| 4,662,914 A | 5/1987 | Hansen | |
| 4,861,988 A | 8/1989 | Henion | |
| 5,012,052 A | 4/1991 | Hayes | |
| 5,055,677 A | 10/1991 | Amirav | |
| 5,137,553 A | 8/1992 | Dawes | |
| 5,192,865 A | 3/1993 | Zhu | |
| 5,306,412 A | 4/1994 | Whitehouse | |
| 5,352,892 A | 10/1994 | Mordehai | |
| 5,367,163 A | 11/1994 | Otsuka | |
| 5,381,008 A | 1/1995 | Tanner | |
| 5,412,208 A | 5/1995 | Covey | |
| 5,448,062 A | 9/1995 | Cooks | |
| 5,552,599 A | 9/1996 | Giessmann | |
| 5,559,326 A | 9/1996 | Goodley | |
| 5,614,711 A | 3/1997 | Li | |
| 5,624,537 A | 4/1997 | Turner | |
| 5,684,300 A | 11/1997 | Taylor | |
| 5,736,741 A | 4/1998 | Bertsch | |
| 5,788,166 A | 8/1998 | Valaskovic | |
| 5,868,322 A | 2/1999 | Loucks, Jr. | |
| 5,959,297 A | 9/1999 | Weinberg | |
| 5,997,746 A | 12/1999 | Valaskovic | |
| 6,107,628 A | 8/2000 | Smith | |
| 6,124,675 A | 9/2000 | Bertrand | |
| 6,190,559 B1 | 2/2001 | Valaskovic | |
| 6,225,623 B1 | 5/2001 | Turner | |
| 6,297,499 B1 | 10/2001 | Fenn | |
| 6,359,275 B1 | 3/2002 | Bertsch | |
| 6,395,183 B1 | 5/2002 | Valaskovic | |
| 6,562,211 B1 | 5/2003 | Kunnecke | |
| 6,583,408 B2 | 6/2003 | Smith | |
| 6,600,155 B1 | 7/2003 | Andrien, Jr. | |
| 6,646,256 B2 | 11/2003 | Gourley | |
| 6,649,907 B2 | 11/2003 | Ebeling | |
| 6,670,608 B1 | 12/2003 | Taylor | |
| 6,690,006 B2 | 2/2004 | Valaskovic | |
| 6,713,757 B2 * | 3/2004 | Tanner et al. | 250/288 |
| 6,717,139 B2 | 4/2004 | Taniguchi | |
| 6,723,985 B2 | 4/2004 | Schultz | |
| 6,744,041 B2 | 6/2004 | Sheehan | |
| 6,744,046 B2 | 6/2004 | Valaskovic | |
| 6,784,424 B1 | 8/2004 | Willoughby | |
| 6,794,642 B2 * | 9/2004 | Bateman et al. | 250/281 |
| 6,803,565 B2 | 10/2004 | Smith | |
| 6,806,468 B2 | 10/2004 | Laiko | |
| 6,818,889 B1 | 11/2004 | Sheehan | |
| 6,861,647 B2 | 3/2005 | Reilly | |
| 6,875,980 B2 * | 4/2005 | Bateman et al. | 250/292 |
| 6,878,930 B1 | 4/2005 | Willoughby | |
| 6,888,132 B1 | 5/2005 | Sheehan | |
| 6,914,243 B2 | 7/2005 | Sheehan | |
| 6,943,347 B1 | 9/2005 | Willoughby | |
| 6,949,739 B2 | 9/2005 | Franzen | |
| 6,949,740 B1 | 9/2005 | Sheehan | |
| 6,949,741 B2 * | 9/2005 | Cody et al. | 250/288 |
| 6,956,205 B2 | 10/2005 | Park | |
| 6,977,372 B2 | 12/2005 | Valaskovic | |
| 6,979,816 B2 | 12/2005 | Tang | |
| 6,987,264 B1 * | 1/2006 | Whitehouse et al. | 250/292 |
| 6,992,299 B2 | 1/2006 | Lee | |
| 7,015,466 B2 | 3/2006 | Takats | |
| 7,019,289 B2 * | 3/2006 | Wang | 250/290 |
| 7,034,292 B1 * | 4/2006 | Whitehouse et al. | 250/289 |
| 7,041,972 B2 | 5/2006 | Bajic | |
| 7,049,584 B1 * | 5/2006 | Whitehouse et al. | 250/288 |
| 7,064,317 B2 | 6/2006 | McCluckey | |
| 7,071,464 B2 * | 7/2006 | Reinhold | 250/282 |
| 7,081,618 B2 | 7/2006 | Laprade | |
| 7,081,621 B1 | 7/2006 | Willoughby | |
| 7,095,019 B1 | 8/2006 | Sheehan | |
| 7,112,785 B2 | 9/2006 | Laramee | |
| 7,138,626 B1 | 11/2006 | Karpetsky | |
| 7,157,698 B2 * | 1/2007 | Makarov et al. | 250/281 |
| 7,161,145 B2 | 1/2007 | Oser | |
| 7,196,525 B2 | 3/2007 | Sparkman | |
| 7,247,495 B2 * | 7/2007 | Amirav | 436/173 |
| 7,253,406 B1 | 8/2007 | Sheehan | |
| 7,332,345 B2 * | 2/2008 | Darrach et al. | 436/173 |
| 7,423,261 B2 | 9/2008 | Truche | |
| 7,429,731 B1 | 9/2008 | Karpetsky | |
| 7,544,933 B2 | 6/2009 | Cooks | |
| 7,569,812 B1 | 8/2009 | Karpetsky | |
| 7,582,864 B2 * | 9/2009 | Verentchikov | 250/290 |
| 7,700,913 B2 | 4/2010 | Musselman | |
| 7,705,297 B2 | 4/2010 | Musselman | |
| 7,714,281 B2 | 5/2010 | Musselman | |
| 7,777,181 B2 | 8/2010 | Musselman | |
| 7,858,926 B1 * | 12/2010 | Whitehouse et al. | 250/281 |
| 7,893,408 B2 | 2/2011 | Hieftje | |
| 7,923,681 B2 * | 4/2011 | Collings et al. | 250/282 |
| 7,928,364 B2 | 4/2011 | Musselman | |
| 7,929,138 B1 | 4/2011 | Webb | |
| 7,982,185 B2 | 7/2011 | Whitehouse | |
| 8,003,935 B2 | 8/2011 | Robinson | |
| 8,026,477 B2 | 9/2011 | Musselman | |
| 8,044,346 B2 | 10/2011 | Kostiainen | |
| RE43,078 E | 1/2012 | Cody | |
| 8,101,910 B2 * | 1/2012 | Loboda | 250/292 |
| 8,207,497 B2 | 6/2012 | Musselman | |
| 8,217,341 B2 | 7/2012 | Musselman | |
| 8,242,459 B2 | 8/2012 | Sun | |
| 8,278,619 B2 * | 10/2012 | Makarov et al. | 250/282 |
| 8,304,718 B2 | 11/2012 | Ouyang | |
| 8,308,339 B2 | 11/2012 | Karpetsky | |
| 8,334,507 B1 * | 12/2012 | Whitehouse et al. | 250/292 |
| 8,362,418 B2 | 1/2013 | Xu | |
| 8,410,431 B2 | 4/2013 | Ouyang | |
| 8,481,922 B2 * | 7/2013 | Musselman | 250/281 |
| 8,487,245 B2 * | 7/2013 | Fernandez et al. | 250/288 |
| 8,525,109 B2 * | 9/2013 | Musselman | 250/288 |
| 2002/0005478 A1 | 1/2002 | Hillenkamp | |
| 2002/0121596 A1 | 9/2002 | Laiko | |
| 2002/0121598 A1 | 9/2002 | Park | |
| 2002/0162967 A1 * | 11/2002 | Atkinson et al. | 250/425 |
| 2002/0185593 A1 | 12/2002 | Doring | |
| 2002/0185595 A1 | 12/2002 | Smith | |
| 2002/0185606 A1 | 12/2002 | Smith | |
| 2003/0052268 A1 | 3/2003 | Doroshenko | |
| 2004/0094706 A1 | 5/2004 | Covey | |
| 2004/0129876 A1 | 7/2004 | Franzen | |
| 2004/0159784 A1 | 8/2004 | Doroshenko | |
| 2004/0169137 A1 | 9/2004 | Westphall | |
| 2005/0079631 A1 | 4/2005 | Laiko | |
| 2005/0230635 A1 | 10/2005 | Takats | |
| 2005/0236374 A1 | 10/2005 | Blankenship | |
| 2005/0236565 A1 | 10/2005 | Oser | |
| 2006/0071665 A1 | 4/2006 | Blake | |
| 2006/0079002 A1 | 4/2006 | Gologan | |
| 2006/0097157 A1 | 5/2006 | Ouyang | |
| 2006/0163468 A1 | 7/2006 | Wells | |
| 2006/0249671 A1 | 11/2006 | Karpetsky | |
| 2006/0266941 A1 | 11/2006 | Vestal | |
| 2007/0114389 A1 | 5/2007 | Karpetsky | |
| 2007/0187589 A1 | 8/2007 | Cooks | |
| 2007/0228271 A1 | 10/2007 | Truche | |
| 2007/0278397 A1 | 12/2007 | Bateman | |
| 2008/0073548 A1 | 3/2008 | Denton | |
| 2008/0156985 A1 | 7/2008 | Venter | |
| 2008/0202915 A1 | 8/2008 | Hieftje | |
| 2009/0272893 A1 | 11/2009 | Hieftje | |
| 2010/0078550 A1 | 4/2010 | Wiseman | |
| 2010/0102222 A1 | 4/2010 | Musselman | |
| 2010/0140468 A1 | 6/2010 | Musselman | |
| 2010/0294925 A1 | 11/2010 | Musselman | |
| 2010/0301209 A1 | 12/2010 | Ouyang | |
| 2011/0042560 A1 | 2/2011 | Ouyang | |
| 2011/0101216 A1 | 5/2011 | Musselman | |
| 2012/0006983 A1 | 1/2012 | Cody | |

(56) References Cited

U.S. PATENT DOCUMENTS

| | | | |
|---|---|---|---|
| 2012/0119082 A1* | 5/2012 | Musselman | 250/288 |
| 2012/0145890 A1 | 6/2012 | Goodlett | |
| 2012/0199735 A1* | 8/2012 | Krechmer et al. | 250/286 |
| 2012/0208004 A1* | 8/2012 | Wolcott et al. | 428/315.7 |
| 2012/0223226 A1* | 9/2012 | Rafferty et al. | 250/288 |
| 2012/0273675 A1* | 11/2012 | Musselman | 250/288 |
| 2012/0280119 A1 | 11/2012 | Musselman | |
| 2012/0295276 A1 | 11/2012 | Cooks | |
| 2012/0312979 A1 | 12/2012 | Cooks | |
| 2012/0312980 A1* | 12/2012 | Whitehouse | 250/282 |
| 2013/0020482 A1 | 1/2013 | Enke | |
| 2013/0037710 A1* | 2/2013 | Wu | 250/287 |
| 2013/0280812 A1* | 10/2013 | Krechmer et al. | 436/71 |

FOREIGN PATENT DOCUMENTS

| | | |
|---|---|---|
| JP | 50-106694 | 8/1975 |
| JP | 51-120288 | 10/1976 |
| JP | 52-91494 | 8/1977 |
| JP | 60-41748 | 3/1985 |
| JP | 2005-150027 | 6/2005 |
| WO | WO03025973 | 3/2003 |
| WO | WO03081205 | 10/2003 |
| WO | WO2004068131 | 8/2004 |
| WO | WO2005094389 | 10/2005 |
| WO | WO2005104182 | 11/2005 |
| WO | WO2007/103693 | 9/2007 |
| WO | WO2007/140349 | 12/2007 |
| WO | WO2007/140351 | 12/2007 |
| WO | WO2008/046111 | 4/2008 |
| WO | WO2008/054393 | 5/2008 |
| WO | WO2008/082603 | 7/2008 |
| WO | WO2009/023361 | 2/2009 |
| WO | WO2011/072130 | 6/2011 |
| WO | WO2011/106656 | 9/2011 |

OTHER PUBLICATIONS

Cody, R.B. et al., "Versatile New Ion Source for the Analysis of Materials in Open Air under Ambient Conditions" Anal. Chem., 2005, 77, 2297-2302.

Cooks, R.G. et al., "Ambient Mass Spectrometry", Science, 2006, 311, 1566-1570.

Dalton, C.N. et al., "Electrospray-Atmospheric Sampling Glow Discharge Ionization Source for the Direct Analysis of Liquid Samples", Analytical Chemistry, Apr. 1, 2003, vol. 75, No. 7, pp. 1620-1627.

Fenn et al., "Electrospray Ionization for Mass Spectrometry of Large Biomolecules," Science, vol. 246, No. 4926, Oct. 6, 1989, pp. 64-71.

Garimella, S. et al., "Gas-flow assisted ion transfer for mass spectrometry", J. Mass Spectrom. 2012, 17, 201-207.

Guzowski, J.P. Jr. et al., "Development of a Direct Current Gas Sampling Glow Discharge Ionization Source for the Time-of-Flight Mass Spectrometer", J. Anal. At. Spectrom., 14, 1999, pp. 1121-1127.

Haddad, R., et al., "Easy Ambient Sonic-Spray Ionization Mass Spectrometry Combined with Thin-Layer Chromatography," Analytical Chemistry, vol. 80, No. 8, Apr. 15, 2008, pp. 2744-2750.

Hill, C.A. et al., "A pulsed corona discharge switchable high resolution ion mobility spectrometer-mass spectrometer", Analyst, 2003, 128, pp. 55-60.

Hiraoka, K. et al., "Atmospheric-Pressure Penning Ionization Mass Spectrometry", Rapid Commun. Mass Spectrom., 18, 2004, pp. 2323-2330.

Hites, Gas Chromatography Mass Spectrometry, Chapter 39, Jun. 24, 1997, pp. 609-626.

Karas, M. et al., "Laser desorption ionization of proteins with molecular masses exceeding 10,000 daltons" Anal. Chem. 1988, 60, 2299-2301.

Kojiro, D.R. et al., "Determination of $C_1$-$C_4$ Alkanes by Ion Mobility Spectrometry", Anal. Chem., 63, 1991, pp. 2295-2300.

Leymarie, N. et al., "Negative Ion Generation Using a MAB Source", presented at the Annual Meeting of the American Society of Mass Spectrometry, 2000.

McLuckey, S.A. et al., "Atmospheric Sampling Glow Discharge Ionization Source for the Determination of Trace Organic Compounds in Ambient Air", Anal. Chem., 60, 1988, pp. 2220-2227.

Otsuka, K. et al., "An Interface for Liquid Chromatograph/Liquid Ionization Mass Spectrometer", Analytical Sciences, Oct. 1988, vol. 4, pp. 467-472.

Takáts et al., "Mass Spectrometry Sampling Under Ambient Conditions with Desorption Electrospray Ionization," Science, vol. 306, No. 5695, Oct. 15, 2004, pp. 471-473.

Tanaka, K. et al., "Protein and polymer analyses up to m/z 100,000 by laser ionization time-of-flight", Rapid Commun. Mass Spectrom., 1988, 2, 151-153.

Tembreull, R., et al., "Pulsed Laser Desorption with Resonant Two-Photon Ionization Detection in Supersonic Beam Mass Spectrometry," Anal. Chem., vol. 58, 1986, pp. 1299-1303, p. 1299.

Zhao, J. et al., Liquid Sample Injection Using an Atmospheric Pressure Direct Current Glow Discharge Ionization Source, Analytical Chemistry, Jul. 1, 1992, vol. 64, No. 13, pp. 1426-1433.

International Search Report, Application No. PCT/US2007/63006, Feb. 5, 2008.

Extended European Search Report, Application No. 07757665.0 PCT/US2007/063006 Jan. 7, 2010, 8 pages.

Article 94(3) European Communication, Application No. 07757665.0 PCT/US2007/063006, Mar. 14, 2012, 9 pages.

International Search Report, Application No. PCT/US2007/69823, Feb. 15, 2008.

Extended European Search Report, Application No. 07797812.0 PCT/US2007/069823, Apr. 4, 2010, 9 pages.

Article 94(3) European Communication, Application No. 07797812.0 PCT/US2007/069823, Jul. 27, 2012, 9 pages.

International Search Report, Application No. PCT/US2007/69821, Feb. 7, 2008.

Extended European Search Report, Application No. 07797811.2 PCT/US2007/069821, Mar. 25, 2010, 9 pages.

European Summons, Application No. 07797811.2 PCT/US2007/069821, Feb. 18, 2013, 39 pages.

International Search Report, Application No. PCT/US2007/81439, Mar. 20, 2008.

Extended European Search Report, Application No. 07844307.4 PCT/US2007/081439, Apr. 14, 2010, 12 pages.

Japanese Office Action, Application No. 2008-558459 PCT/US2007/063006, Jan. 19, 2012, 4 pages.

Unofficial Translation of Japanese Office Action, Application No. 2008-558459 PCT/US2007/063006, Jan. 19, 2012, 5 pages.

Chinese Office Action, Application No. 200780015974.5 PCT/US2007/063006, Feb. 2, 2012, 5 pages.

Chinese Office Action, Application No. 200780015974.5 PCT/US2007/063006, Sep. 25, 2012, 8 pages.

Chinese Office Action, Application No. 200780015974.5 PCT/US2007/063006, Dec. 26, 2012, 7 pages.

The AccuTOF-DART Mass Spectrometer, Jan. 1, 2006, pp. 1-6; www.jeolusa.com/SERVICESUPPORT/ApplicationsResources/AnalyticalInstruments/Documents/Downloads/tabid/337/DMXModule/693/CommandCore_Download/Default.aspx?EntryId=171.

Busch, Kenneth L., Desorption Ionization Mass Spectrometry, J. Mass Spectrometry, vol. 30, pp. 233-240 (1995).

Harris, Glenn A. et al., Ambient Sampling/Ionization Mass Spectrometry: Applications and Current Trends, Apr. 15, 2011, Anal. Chem. 2011, 83, pp. 4508-4538.

Harris, Glenn A. et al., Simulations and Experimental Investigation of Atmospheric Transport in an Ambient Metastable-Induced Chemical Ionization Source, Anal. Chem. 2009, 81, pp. 322-329.

Kauppila, Tiina J., et al., Desorption atmospheric pressure photoionization—mass spectrometry in routine analysis of confiscated drugs, Forensic Science International 210 (2011) pp. 206-212.

Oral Proceedings European Communication, Application No. 07757665.0 PCT/US2007/063006, Mar. 9, 2013, 5 pages.

Korean Patent Application 7024130/2008, Jun. 29, 2013, 6 pages.

Article 94(3) European Communication, Application No. 07797811.2 PCT/US2007/069821, Feb. 2, 2012, 8 pages.

Summons Application No. 07797811.2 PCT/US2007/069821, Feb. 18, 2013, 12 pages.

International Search Report, Application No. PCT/US2012/000061, Aug. 6, 2013.

* cited by examiner

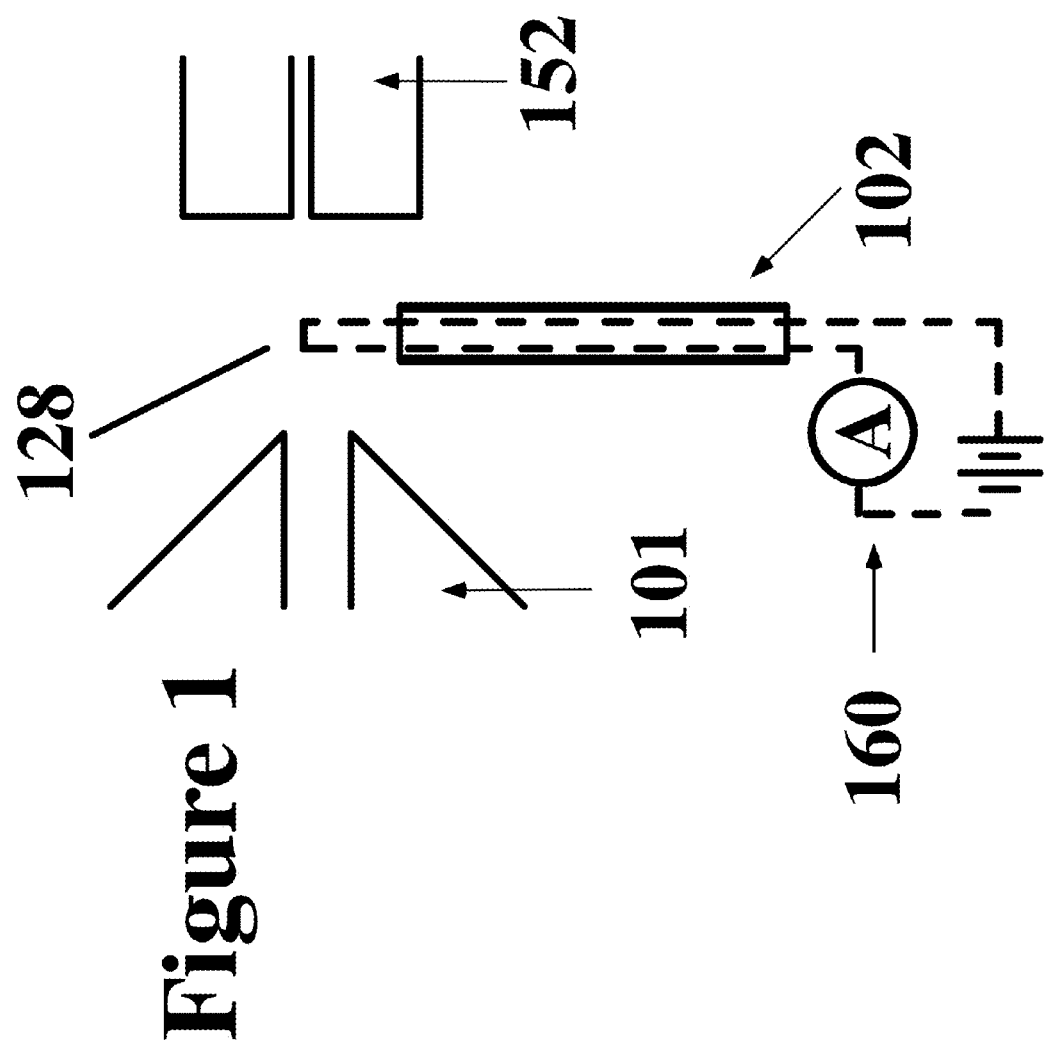

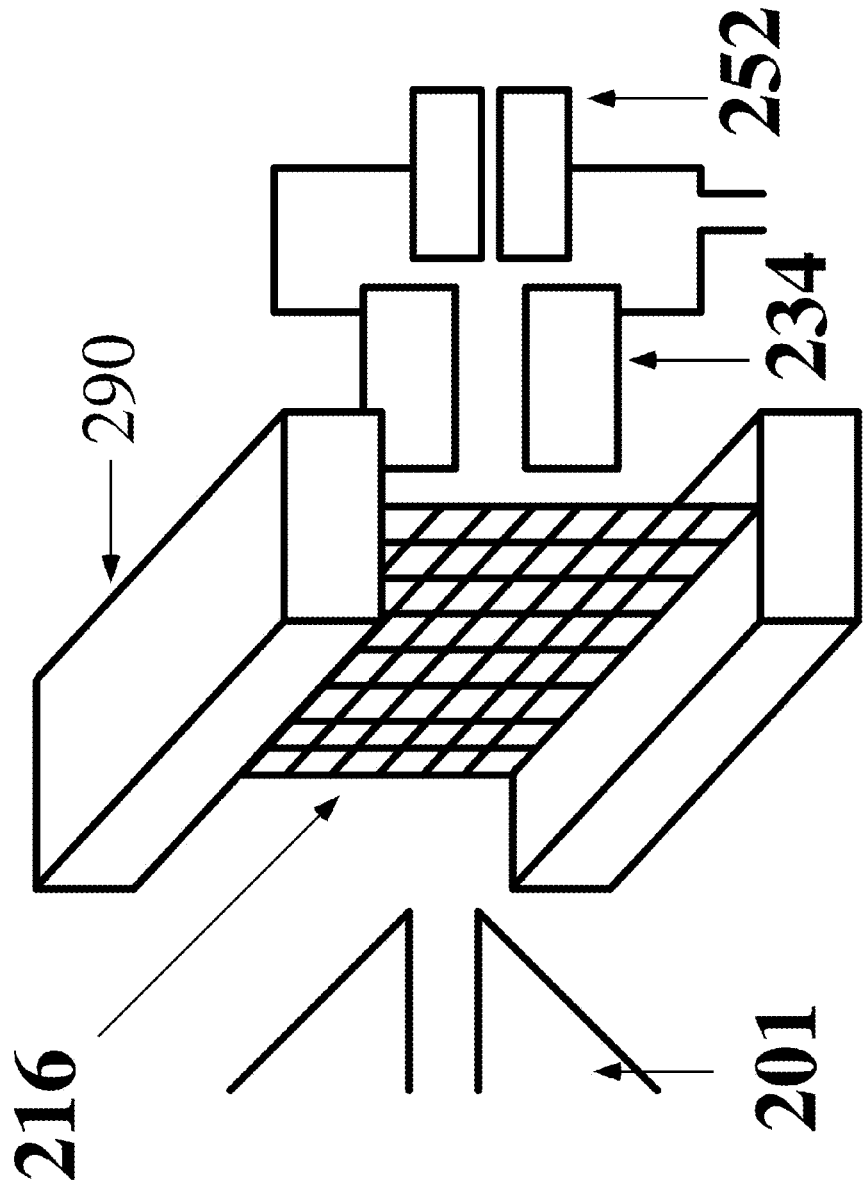

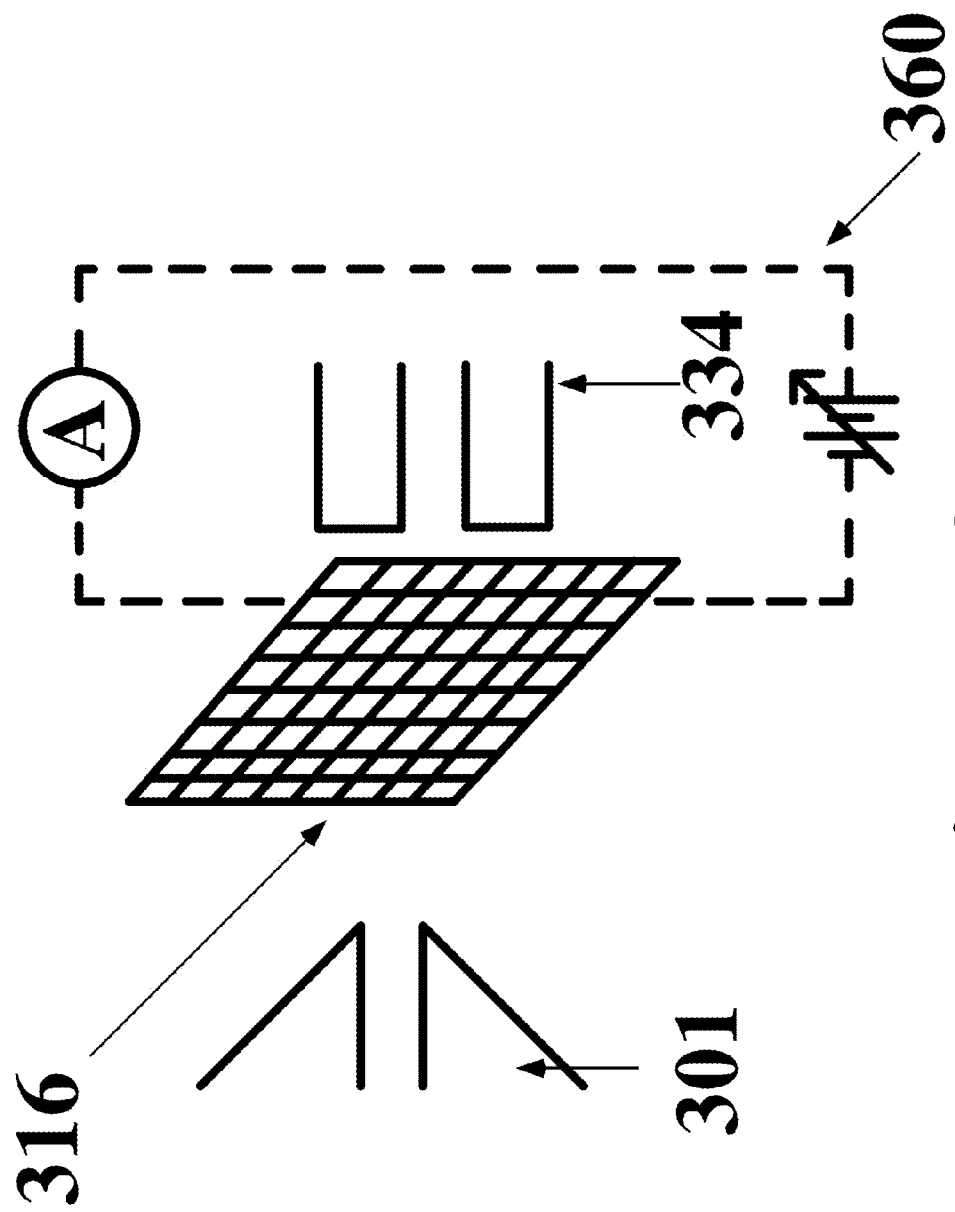

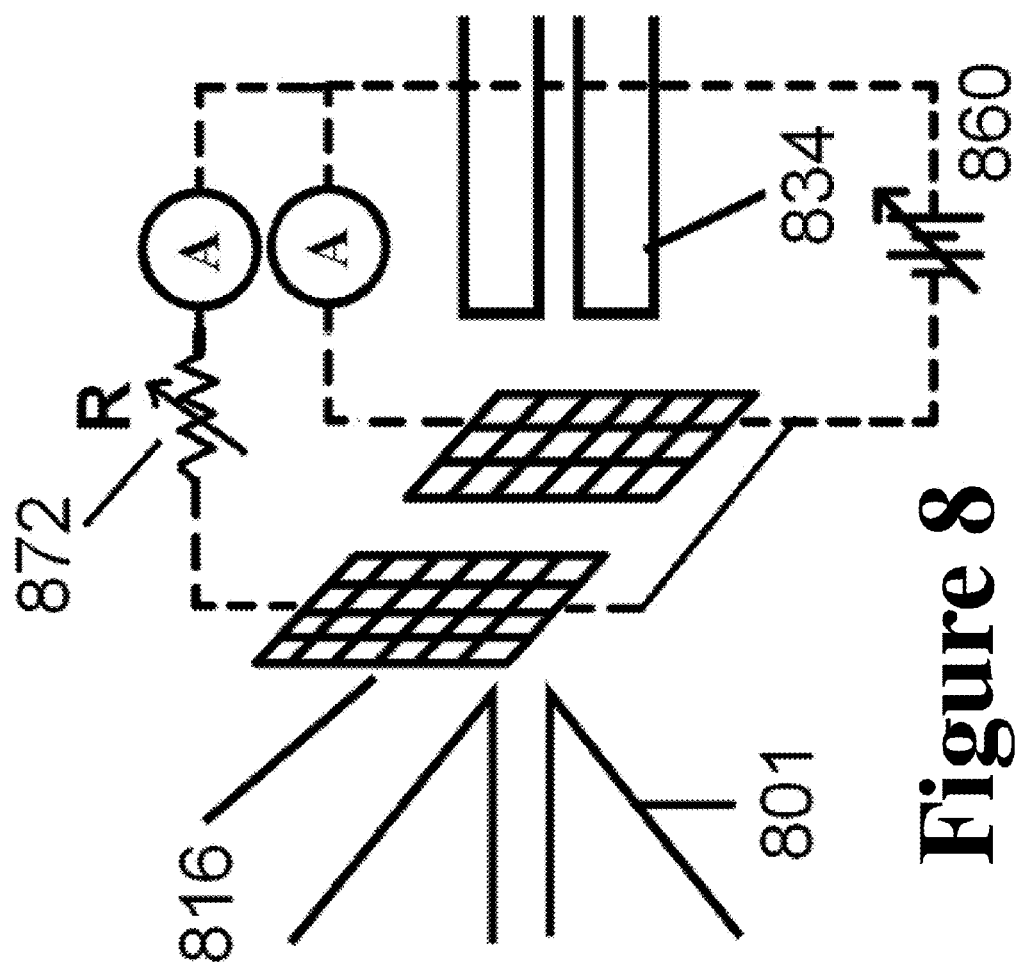

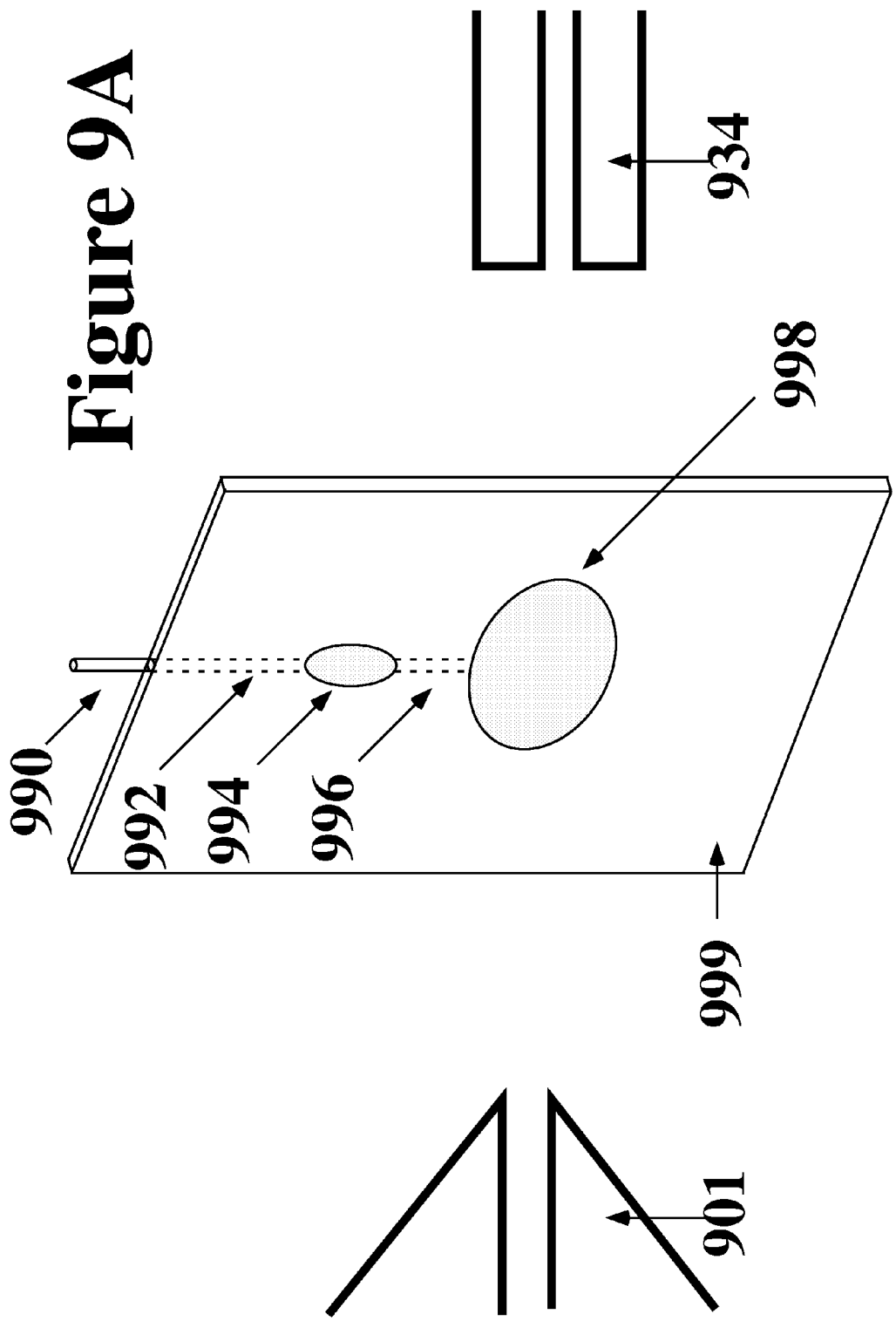

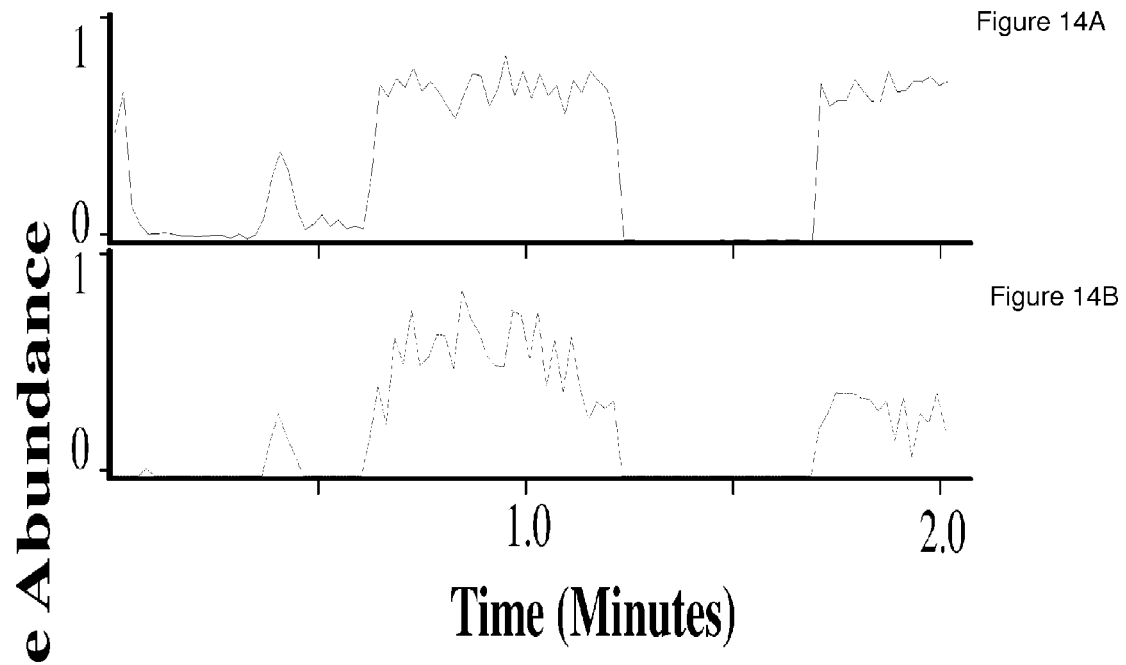
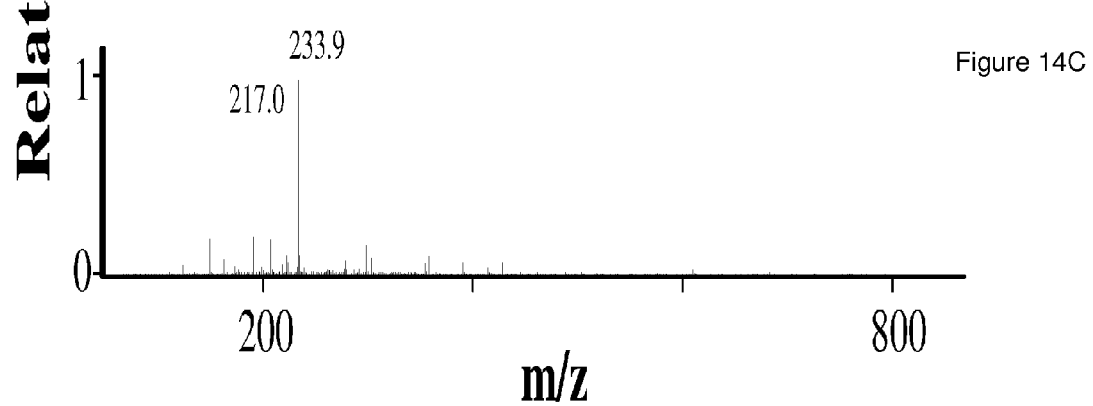
Figure 14A
Figure 14B
Figure 14C

APPARATUS AND METHOD FOR THERMAL ASSISTED DESORPTION IONIZATION SYSTEMS

PRIORITY CLAIM

This application is a continuation of (1) U.S. patent application Ser. No. 13/364,322 entitled "APPARATUS AND METHOD FOR THERMAL ASSISTED DESORPTION IONIZATION SYSTEMS", inventors: Jordan Krechmer and Brian D. Musselman, filed Feb. 2, 2012 which claims priority to (2) U.S. Provisional Patent Application No. 61/439,866 entitled "APPARATUS FOR THERMAL ASSISTED DESORPTION IONIZATION", inventors Jordan Krechmer and Brian D. Musselman, filed Feb. 5, 2011; (3) U.S. Provisional Patent Application No. 61/582,204 and entitled "APPARATUS AND METHOD FOR THERMAL ASSISTED DESORPTION IONIZATION SYSTEMS" by, inventors Jordan Krechmer and Brian D. Musselman, filed Dec. 30, 2011, the contents of each of which are incorporated herein by reference in their entireties, and (4) U.S. Provisional Patent Application No. 61/587,218 and entitled "APPARATUS AND METHOD FOR THERMAL ASSISTED DESORPTION IONIZATION SYSTEMS", inventors Jordan Krechmer and Brian D. Musselman, filed Jan. 17, 2012, the contents of each of which ((1)-(4)) are herein incorporated by reference in their entireties.

FIELD OF THE INVENTION

The present invention relates to methods and devices for controlling the kinetic energy and/or the efficiency of desorption of neutral molecules from a surface.

BACKGROUND OF THE INVENTION

Development of devices for desorption ionization of molecules direct from solids, and liquids in open air using a direct analysis in real time (DART) source has previously been described in U.S. Pat. No. 6,949,741 "Atmospheric Pressure Ionization Source" which is expressly incorporated by reference in its entirety. DART uses a heated carrier gas to effect desorption of sample into that same carrier gas where gas phase ionization occurs. Unfortunately, the heating of the carrier gas to a sufficient temperature to enable desorption of some analytes takes considerable time. Further, the transfer of heat to the sample by that gas is not very efficient. A gas ion separator described in U.S. Pat. No. 7,700,913, "Sampling system for use with surface ionization spectroscopy" which is expressly incorporated by reference in its entirety can be used to improve the efficiency of sampling.

SUMMARY OF THE INVENTION

In various embodiments of the present invention, a mesh can be placed between the source of ionizing gas, which can be at atmospheric pressure, and the inlet of a spectrometer. The mesh can be made from a conductive material and can carry an electrical current. In an embodiment of the invention a sample can be deposited directly onto the mesh. A current can be applied to the mesh in order to heat the wire. Sample related molecules can be desorbed from or in close proximity to the mesh. The desorbed molecules can interact with the ionizing gas in the region between the mesh and the atmospheric pressure ionization (API)-inlet of a spectrometer. The ions that are formed from this interaction can enter the spectrometer for analysis. In an embodiment of the present invention, the desorbed molecules can enter the high pressure region of a spectrometer by the action of an electrical field as in the case of an ion mobility spectrometer (IMS). The ions formed in the region immediately adjacent to the wire mesh which in this case has a potential equivalent to the end of the IMS enter the IMS spectrometer for analysis.

In various embodiments of the present invention, a mesh can be placed between the source of ionizing gas, which can be at atmospheric pressure, and the inlet of a spectrometer. The mesh can be made from a conductive material and can carry an electrical current. In various embodiments of the invention a sample can be deposited directly onto the mesh. A current can be applied to the mesh in order to heat the wire desorbing ions and neutrals of the sample into the atmospheric pressure region.

Sample related molecules can be desorbed from or in close proximity to the mesh. The desorbed molecules can interact with the ionizing gas in the region between the mesh and the atmospheric pressure ionization (API)-inlet of a spectrometer. The ions that are formed near to the wire mesh from this interaction can enter the spectrometer for analysis at atmospheric pressure or at a pressure that are higher than atmospheric when electrical potentials are able to draw or push those ions into the volume of the spectrometer.

In various embodiments of the present invention, two or more mesh can be placed between the source of ionizing gas, which can be at atmospheric pressure, and the inlet of a spectrometer. The two or more mesh can be made from a conductive material and can carry an electrical current. In various embodiments of the invention two or more samples can be deposited directly onto two or more of the mesh. A current can be applied to the two or more of the sample containing mesh in order to heat the wire mesh desorbing ions and neutrals into the atmospheric pressure region. The kinetic energy of ions desorbed from or in close proximity to the wire mesh can be controlled by modulating the potential applied to adjacent mesh or series of mesh. Control of the ion kinetic energy in the region between the sample laden wire mesh and the atmospheric pressure ionization (API)-inlet of a spectrometer can be used to improve the analysis of the two or more samples. Control of the ion kinetic energy in the region between the sample laden wire mesh and the atmospheric pressure ionization (API)-inlet of a spectrometer is desirable to improve the resolution of the spectrometer. The ions that are formed from this interaction can enter the spectrometer for analysis.

The kinetic energy of ions desorbed from or in close proximity to the wire mesh can be controlled by modulating the potential applied to the adjacent mesh or series of mesh. Control of the ion kinetic energy in the region between the sample laden wire mesh and the atmospheric pressure ionization (API)-inlet of a spectrometer can be used to improve the transfer of ions into the spectrometer for analysis of the one or more samples. Application of an electrical potential to the wire mesh enables limited control of the ion kinetic energy in the region between the sample laden wire mesh and the atmospheric pressure ionization (API)-inlet of a spectrometer which can have either a different electrical potential applied to its surface or be operated at the same potential as that wire mesh. Depending on the configuration of the spectrometer inlet the application of a potential can be used to improve resolution of the spectrometer. The ions that are formed near to the wire mesh can enter the spectrometer for analysis at atmospheric pressure or at a pressure that are higher than atmospheric when electrical potentials are able to draw or push those ions into the volume of the spectrometer.

In various embodiments of the invention, in order to control the ion energy of ions entering an ion mobility spectrometer the wire mesh supporting the ionization can be placed immediately in front of the wire mesh to which potential is being applied in order to control ion kinetic energy. In the case of ion mobility spectrometers it can be necessary to introduce ions at or very close to the potential of at the IMS entrance in order for the ions to enter and be retained by the spectrometer.

In traditional IMS devices ionization of neutral molecules occurs in the volume of the spectrometer. Ions are generated using radioactive particle emission from elements such as $^3$H (tritium), $^{63}$Ni, or other radioactive materials. Plasma-based ionization is also feasible using electrical discharge in the volume of the sampling region in order to produce ions which subsequently interact with the neutral molecules to ionize them in that volume. The production of ions inside of the volume of the IMS reduces the range of ion kinetic energies for the ionized particles since the electrical field is uniform in that region of ionization.

The position of the ionization source relative to the IMS determines a distance over which ions trajectory must follow before entering the IMS. Positioning of the IMS ionization region even a very short distance away from the entrance to the spectroscopy system results in a decline in achievable resolution of the spectroscopy system. In the case of ambient pressure ionization from a heated wire mesh, rapid vaporization of the sample into the carrier gas from the sample laden wire mesh can occur in close proximity to the entrance of the IMS between the carrier gas source, and the inlet of the IMS spectroscopy system. Thus the position of the sample laden wire mesh relative to the entrance of the IMS spectrometer influences the kinetic energy of the ions formed from those desorbed molecules. The kinetic energy distribution of ions that are formed immediately in the vicinity of the wire mesh in close proximity to the IMS can be corrected. As the majority of ions produced in the experiment are produced at or near atmospheric pressure in close proximity to the wire mesh those ions may be formed inside the volume of the ion mobility spectrometer (IMS). The kinetic energy of ions is related to the electrical fields in which they are formed. In the caser of the IMS systems the kinetic energy is thought to be uniform when all ions are formed inside the tube, however in order to effect sampling of ions for spectroscopic analysis a potential is applied to wires that form a Bradbury-Nielson gate a short distance away from the he ionizing region. The distance between the BN-gate and the position where the ions are formed effects their kinetic energy. The ability to change the energy of the ions formed in very close proximity to the IMS entrance improves the control of those ions afforded by the ion focusing of the IMS. Application of a electrical potential to the wire mesh in close proximity to the ionization region therefore will change the ion kinetic energy of those ions that are closer to the wire mesh to a greater degree than those that have been formed further away from the wire mesh. Linking the application of electrical potential applied to the wire mesh with the electrical potential used to open and close the BN-gate enables those ions that are further from the gate to catch up to the ions that are closer thus generating a collection of ions that have a more uniform kinetic energy as they are transferred from the ionization region into the ion separation region of the spectrometer.

In an embodiment of the invention application of a potential to a wire mesh located between a wire mesh from which sample molecules are being desorbed and the entrance the spectrometer to which a different potential applied is used to change the kinetic energy of ions formed in close proximity to that wire mesh.

In an alternative embodiment of the invention application of a small potential to the kinetic energy controlling mesh will result in rejection of the ions by the spectrometer. The action of rejection ions whose kinetic energy is different than those ions formed inside the atmospheric pressure region of the spectrometer can be used to further improve the resolution of the spectrometer as it reduces the kinetic energy of the ions being sampled.

In various embodiments of the invention, in order to complete a more rapid vaporization of the sample into the carrier gas the sample laden mesh can be positioned between the carrier gas source, a gas ion separator and the atmospheric pressure inlet of a spectroscopy system.

In an alternative embodiment of the invention a sample can be deposited onto a second surface that can be placed in close proximity to the mesh through which the ionizing carrier gas can flow. Sample related molecules can be desorbed from the second surface as a result of the current applied to the mesh. Sample related molecules can be desorbed from the second surface as a result of heating of the mesh by increasing the current running through the mesh. In various embodiments of the invention, by increasing the current passed through the wire, increased radiant heating can be generated. In various embodiments of the invention, increased radiant heat can effect desorption of less volatile components in a sample.

In an alternative embodiment of the invention a chemical can be deposited onto a second surface that can be placed in close proximity to the mesh through which the ionizing carrier gas can flow. Molecule of that chemical can be desorbed from the second surface as a result of the current applied to the mesh. In various embodiments of the invention, by increasing the current passed through the wire, increased radiant heating can be generated resulting in vaporization of the chemical into the ionizing region where it might be ionized creating an ion that might ionize other molecules. In various embodiments of the invention, the chemical desorbed from the second surface acts as a dopant for ionizing sample related molecules.

BRIEF DESCRIPTION OF THE DRAWINGS

This invention is described with respect to specific embodiments thereof. Additional aspects can be appreciated from the Figures in which:

FIG. 1 is a schematic diagram of a sampling probe including a heated filament for sample desorption positioned between a source for ionizing gas and the atmospheric pressure inlet of a spectrometer;

FIG. 2 is a schematic diagram of a sampling system incorporating the mesh as a sample support for desorption ionization positioned between a source for ionizing gas and a gas ion separator positioned before the atmospheric pressure inlet of a spectrometer, according to an embodiment of the invention;

FIG. 3 is a schematic diagram of a sampling system incorporating a power supply to heat the mesh positioned between the ionizing gas source and a gas ion separator where analyte has been placed on the mesh;

FIG. 8 is a schematic diagram of a sampling system incorporating an ionizing gas source with two mesh pieces heated with a single power supply, wherein the meshes are positioned between the ionizing gas source and the sample to be analyzed where the sample is positioned in close proximity to a gas ion separator which permits transfer of ions to the API-inlet region of the mass spectrometer according to an embodiment of the invention;

FIGS. 9A-D are schematic diagrams of a sampling system incorporating an ionizing gas source with a mesh associated with a card and a reservoir, wherein the mesh is positioned between the ionizing gas source and a gas ion separator which permits transfer of ions to the API-inlet region of the mass spectrometer according to an embodiment of the invention;

FIG. 14A shows a total ion chromatogram (TIC) over the time interval zero to two minutes obtained using a DART carrier gas temperature of 50 degrees Centigrade while rapidly increasing the current passing through the mesh supporting the sample applied to a foam sponge plastic from 0 Amps at time=0, to 6 Amps at time=30 second; FIG. 14B shows a partial mass chromatogram of the 195 Dalton ion produced during the two minute analysis shown in FIG. 14A; and FIG. 14C shows the mass spectrum obtained by summing the spectra obtained between 0.68-1.08 minutes of the TIC shown in FIG. 14A;

DETAILED DESCRIPTION OF THE INVENTION

Definitions

Figure 4A:
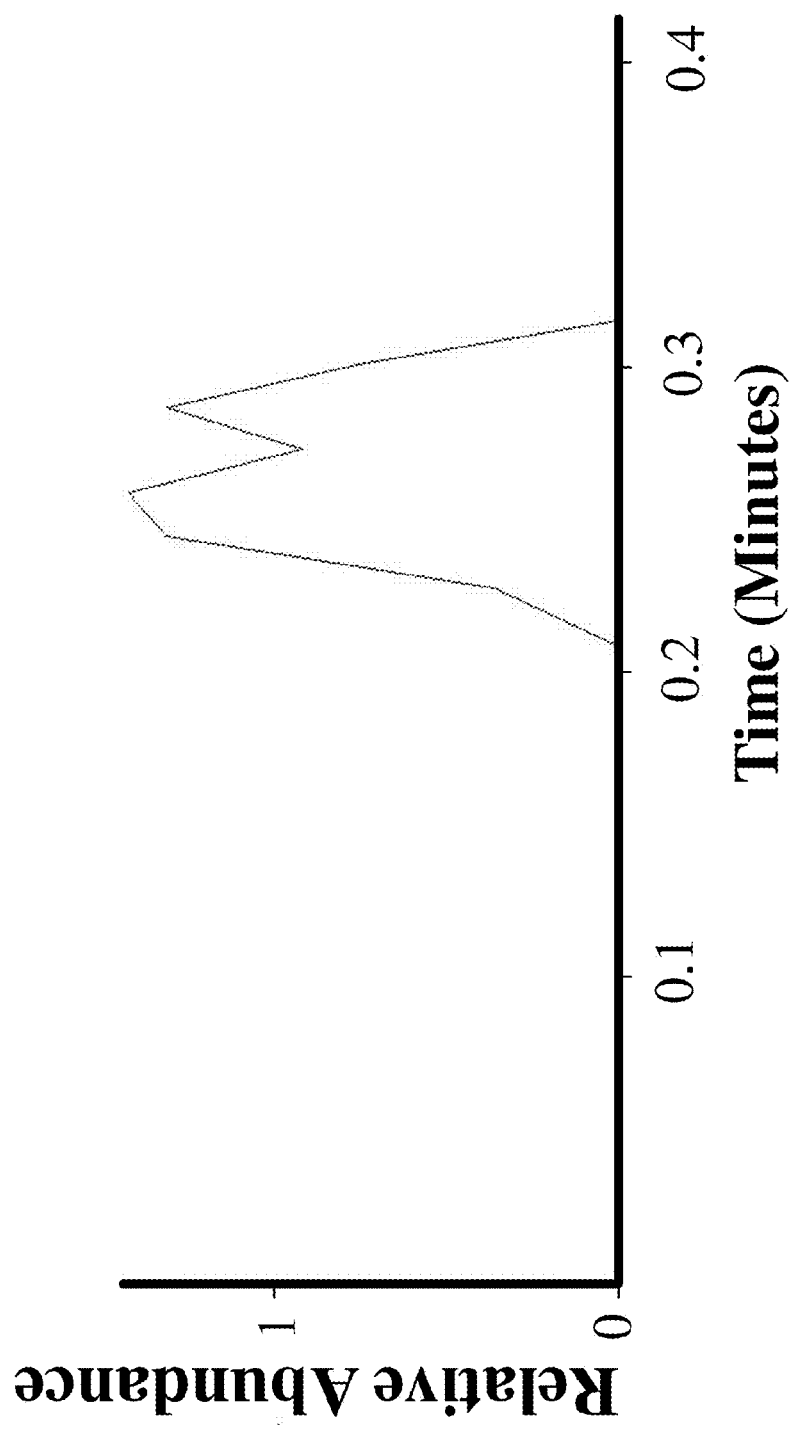
FIG. 4A shows a partial mass chromatogram of the 325 Dalton ion produced during analysis and FIG. 4B shows the mass spectrum containing the molecular ion for quinine at 325 Daltons obtained using a DART carrier gas temperature of 50 degrees Centigrade while rapidly increasing the current passing through the mesh supporting the sample from 0 Amps at time=0, to 6 Amps at time=30 seconds.

The transitional term "comprising" is synonymous with "including," "containing," or "characterized by," is inclusive or open-ended and does not exclude additional, unrecited elements or method steps.

The transitional phrase "consisting of" excludes any element, step, or ingredient not specified in the claim, but does not exclude additional components or steps that are unrelated to the invention such as impurities ordinarily associated with a composition.

The transitional phrase "consisting essentially of" limits the scope of a claim to the specified materials or steps and those that do not materially affect the basic and novel characteristic(s) of the claimed invention.

A vacuum of atmospheric pressure is 1 atmosphere=760 torr. Generally, 'approximately' in this pressure range encompasses a range of pressures from below $10^1$ atmosphere=7.6× $10^3$ torr to $10^{-1}$ atmosphere=7.6×$10^1$ torr. A vacuum of below $10^{-3}$ torr would constitute a high vacuum. Generally, 'approximately' in this pressure range encompasses a range of pressures from below $5\times10^{-3}$ torr to $5\times10^{-6}$ torr. A vacuum of below $10^{-6}$ trr would constitute a very high vacuum. Generally, 'approximately' in this pressure range encompasses a range of pressures from below $5\times10^{-6}$ torr to $5\times10^{-9}$ torr. In the following, the phrase 'high vacuum' encompasses high vacuum and very high vacuum. The prime function of the gas ion separator is to remove the carrier gas while increasing the efficiency of transfer of neutral molecules including analyte molecules into the mass spectrometer. When constructed from non conducting material, the gas ion separator can also be used to insulate or shield the high voltage applied to the inlet of the mass spectrometer.

A filament means one or more of a loop of wire, a segment of wire, a metal ribbon, a metal strand or an un-insulated wire, animal string, paper, perforated paper, fiber, cloth, silica, plastic, plastic foam, polymer, teflon, polymer impregnated teflon, cellulose and hydrophobic support material coated and impregnated filaments.

A metal comprises one or more elements consisting of lithium, beryllium, boron, carbon, nitrogen, oxygen, sodium, magnesium, aluminum, silicon, phosphorous, sulphur, potassium, calcium, scandium, titanium, vanadium, chromium, manganese, iron, cobalt, nickel, copper, zinc, gallium, germanium, arsenic, selenium, rubidium, strontium, yttrium, zirconium, niobium, molybdenum, technetium, ruthenium, rhodium, palladium, silver, cadmium, indium, tin, antimony, tellurium, cesium, barium, lanthanum, cerium, praseodymium, neodymium, promethium, samarium, europium, gadolinium, terbium, dysprosium, holmium, erbium, thulium, ytterbium, lutetium, hafnium, tantalum, tungsten, rhenium, osmium, iridium, platinum, gold, mercury, thallium, lead, bismuth, polonium, francium and radium.

A plastic comprises one or more of polystyrene, high impact polystyrene, polypropylene, polycarbonate, low density polyethylene, high density polyethylene, polypropylene, acrylonitrile butadiene styrene, polyphenyl ether alloyed with high impact polystyrene, expanded polystyrene, polyphenylene ether and polystyrene impregnated with pentane, a blend of polyphenylene ether and polystyrene impregnated with pentane or polyethylene and polypropylene.

A polymer comprises a material synthesized from one or more reagents selected from the group comprising of styrene, propylene, carbonate, ethylene, acrylonitrile, butadiene, vinyl chloride, vinyl fluoride, ethylene terephthalate, terephthalate, dimethyl terephthalate, bis-beta-terephthalate, naphthalene dicarboxylic acid, 4-hydroxybenzoic acid, 6-hyderoxynaphthalene-2-carboxylic acid, mono ethylene glycol (1,2 ethanediol), cyclohexylene-dimethanol, 1,4-butanediol, 1,3-butanediol, polyester, cyclohexane dimethanol, terephthalic acid, isophthalic acid, methylamine, ethylamine, ethanolamine, dimethylamine, hexamthylamine diamine (hexane-1,6-diamine), pentamethylene diamine, methylethanolamine, trimethylamine, aziridine, piperidine, N-methylpiperideine, anhydrous formaldehyde, phenol, bisphenol A, cyclohexanone, trioxane, dioxolane, ethylene oxide, adipoyl chloride, adipic, adipic acid (hexanedioic acid), sebacic acid, glycolic acid, lactide, caprolactone, aminocaproic acid and or a blend of two or more materials synthesized from the polymerization of these reagents.

A plastic foam means a polymer or plastic in which a bubble containing a gas is trapped including polyurethane, expanded polystyrene, phenolic foam, XPS foam and quantum foam.

A mesh means one or more of two or more connected filaments, two or more connected strings, foam, a grid, perforated paper, screens, paper screens, plastic screens, fiber screens, cloth screens, polymer screens, silica screens, Teflon screens, polymer impregnated Teflon screens, cellulose screens and hydrophobic support material coated or impregnated mesh. In various embodiments of the invention, a mesh includes one or more of three or more connected filaments, three or more connected strings, mesh, foam, a grid, perforated paper, screens, plastic screens, fiber screens, cloth and polymer screens.

Deployed means attached, affixed, adhered, inserted, located or otherwise associated. Thus a paper screen can be deployed on a card where the paper for the screen and the paper for the card are of a unitary construction. A card means a sample holder. A card can be made of one or more of paper, cardboard, insulating materials, conductive materials, plastic, polymers, minerals and metals. A reservoir is a vessel used to contain one or more of a liquid, a gas or a solid sample.

In the following description, various aspects of the present invention will be described. However, it will be apparent to those skilled in the art that the present invention may be practiced with only some or all aspects of the present invention. For purposes of explanation, specific numbers, materials, and configurations are set forth in order to provide a thorough understanding of the present invention. However, it will be apparent to one skilled in the art that the present invention may be practiced without the specific details. In other instances, well-known features are omitted or simplified in order not to obscure the present invention.

Parts of the description will be presented in data processing terms, such as data, selection, retrieval, generation, and so forth, consistent with the manner commonly employed by those skilled in the art to convey the substance of their work to others skilled in the art. As is well understood by those skilled in the art, these quantities (data, selection, retrieval, generation) take the form of electrical, magnetic, or optical signals capable of being stored, transferred, combined, and otherwise manipulated through electrical, optical, and/or biological components of a processor and its subsystems.

Various operations will be described as multiple discrete steps in turn, in a manner that is most helpful in understanding the present invention; however, the order of description should not be construed as to imply that these operations are necessarily order dependent.

Various embodiments will be illustrated in terms of exemplary classes and/or objects in an object-oriented programming paradigm. It will be apparent to one skilled in the art that the present invention can be practiced using any number of different classes/objects, not merely those included here for illustrative purposes.

The invention is illustrated by way of example and not by way of limitation in the figures of the accompanying drawings in which like references indicate similar elements. It should be noted that references to 'an' or 'one' embodiment in this disclosure are not necessarily to the same embodiment, and such references mean at least one.

There remain encumbrances to the employment of the DART technique for a variety of samples and various experimental conditions. Previously, in order to facilitate more comprehensive analysis of samples the DART desorption ionization method utilized heating of the carrier gas, which contains the metastable species. As the carrier gas temperature was increased molecules were vaporized where interaction with the metastable species resulted in ionization of the molecules. This transfer of energy using heated gas limits the efficiency of the analysis process. It results in consumption of large volumes of gas and more significantly adds a significant delay to the time taken for the analysis. The time required to increase the carrier gas temperature by three hundred degrees can be several minutes. In contrast, the time required for collection of the mass spectrum at the optimum temperature can be as short as a second. Enabling more efficient heating using a metal substrate often results in an increase in thermal decomposition of the material of interest. Likewise, employing more efficient heating of the carrier gas is difficult to achieve without negatively affecting the metastable species present in the carrier gas.

In various embodiments of the invention placing sample on a porous surface directly in the path of the carrier gas such that the gas flows through it, the so called "transmission-DART" configuration results in a method that does not require heating of the ionizing gas. In various embodiments of the invention, the transmission-DART configuration results in less thermal degradation of the analyte prior to gas phase ionization. In various embodiments of the invention, the transmission-DART configuration results in generation of mass spectra with fewer ions derived from thermal decomposition of the sample than observed in conventional open air ionization experiments. In various embodiments of the invention, the transmission-DART configuration uses significantly lower volumes of gas carrier during the experiment. In various embodiments of the invention, the transmission-DART configuration reduces the function of the carrier gas to providing the metastable species for ionization. In various embodiments of the invention, the transmission-DART configuration heats the porous surface by directing electrical current through a mesh in close proximity to the porous surface which transfers heat to the sample. In various embodiments of the invention, the transmission-DART configuration lowers the carrier gas temperature enabling an increase in spatial resolution of the analysis since only molecules from the heated region vaporize. In various embodiments of the invention, the transmission-DART configuration allows direct heating of specific regions of the mesh to facilitate higher throughput analysis since samples can be placed in closer proximity to each other. In various embodiments of the invention, the application of the transmission-DART configuration to heating of porous surfaces results in more rapid desorption than available by the conventional DART experiment.

In various embodiments of the invention the sample is deposited on a second surface in close proximity to the mesh in order for the heat generated from the application of current to the mesh to cause desorption of molecule from that sample into the gas phase where ionization occurs.

In an alternative embodiment of the present invention, separate aliquots of the sample are placed on separate mesh pieces and placed in close proximity to one another in the presence of the same ionizing gas in order that the temperature of the gas and the temperature of the unheated mesh simultaneously increase to effect desorption of molecules into the gas phase for analysis of the sample. In various embodiments of the invention the mesh is surrounded by a porous material to which sample has been applied for analysis. After positioning the sample in the region between the ionizing gas source and the inlet of the spectrometer a current is applied to the mesh to complete heating of the surrounding material and desorption of molecules into the gas phase for ionization.

Direct Ionization in Real Time (DART) (Cody, R. B., Laramee, J. A., Durst, H. D. "Versatile New Ion Source for the Analysis of Materials in Open Air under Ambient Conditions" Anal. Chem., 2005, 77, 2297-2302 and Desorption Electrospray Surface Ionization (DESI) (Cooks, R. G., Ouyang, Z., Takats, Z., Wiseman, J. M. "Ambient Mass Spectrometry", Science, 2006, 311, 1566-1570; both articles are herein explicitly incorporated by reference in their entireties, are recent developments enabling surface desorption ionization by producing ions in open air for detection with mass spectrometer systems. Since the invention of DART a variety of gas-based open air ionization systems have been demonstrated including but not limited to, Plasma Assisted Desorption/Ionization also known as Dielectric Barrier Discharge Ionization (PADI, DBDI or DCBI), Desorption Atmospheric Pressure Chemical Ionization (DAPCI), Desorption Sonic Spray Ionization (DeSSI), Desorption Atmospheric Pressure Photoionization (DAPPI), and Flowing Atmospheric-Pressure Afterglow (FAPA). The ability to desorb and ionize intact molecules in open air offers a number of advantages for rapid real time analysis of analyte samples. In the case of the DART ionization source, the ability to vary the carrier gas temperature has been used to permit thermal profiling of samples. This application of heat has permitted a more thorough detection of the various components of the sample. This is especially true when the components of the sample have different vapor pressure. Unfortunately due to the resistive character of heaters and the large volume of gas that these methods use to transfer heat into the sample, operation at high temperature involves a number of limitations. For example, waiting for the temperature of the gas exiting the source to increase to a desired temperature can take several minutes slowing the analysis of sample considerably.

Determination of the chemical composition of solid objects or materials present on the surface of those objects is facilitated by removing those materials to a chemical analyzer. Methods for removing chemicals from the surface include the use of heated gas, heat source capable of radiating heat to the surface, application of liquid such as water or solvents to dissolve chemicals present on or comprising the surface. In various embodiments of the invention it is desirable to desorb neutral molecules from a surface by using jets supplying steam or heated water. In various embodiments of the invention, it is desirable to apply a vacuum in the vicinity of the surface to remove the desorbed neutral molecules released from the surface. This combination combines the action of heated water vapor desorbing material from the surface while also applying suction to quickly remove the vapor from the surface area thus avoiding condensation of the liquid back onto the surface.

A problem in chemical analysis is that the use of water can damage many chemical sensors therefore generally speaking the water vapor is condensed and used in the liquid form. For reasons associated with improved analysis throughput and the determination of chemicals that might be present on surfaces that are porous, such as baggage, clothing, cardboard and inside of packaging that might be sealed for purposes of protecting the chemicals inside from analysis a directed jet of heated water vapor or steam can be used to remove molecules from surfaces or in the immediate proximity of surfaces in order to achieve a through chemical analysis.

In many cases containers carrying illicit materials such as narcotics or food are packaged in plastic so as to prevent exposure to liquid or other chemicals. Plastic packaging is not thought to be permeable, however owing to the need to keep the material flexible small molecules defined as plasticizers are an integral part of the composition of that packaging material. The use of plasticizers effectively means that there is a liquid component of the plastic that may move freely from one inside the container to outside the container. Movement of a molecule from one surface to another and back again can be driven by alternating hot and cold treatments to increase the movement of molecules. While plasticizers are generally thought of as inert molecules, they contain functional chemical subunits that are capable of binding and releasing chemicals that they come into contact with, even when the contact period is a short period of time. In various embodiments of the invention, a pulsed jet of heated water vapor can be directed at the outside surface of a plastic package to interrogate the composition of the contents of the plastic package.

In the case of a customs inspection, some chemicals are deemed to be too dangerous to open. Simple economics prevail and often high value chemicals are mislabeled for import to save on duties. The capability to essentially extract an infinitesimal volume of sample with a benign sampling protocol can aid these investigators. In various embodiments of the invention, a jet of heated water vapor can be directed at the outside surface of a plastic package to interrogate the composition of the contents of the plastic package.

Determination of Fatty Acid Content of Triacyl-Glycerides

A method for direct formation of methyl-esters in the heated injector of a gas chromatography instrument demonstrated the potential for bypassing the time consuming saponification step. The experiment incorporated mixing a chemical reagent, tetramethyl ammonium hydroxide, with the analyte followed by injection into the heated volume of the GC injector leading to a simultaneous hydrolysis of the acid and its methylation, a trans-esterification. In an embodiment of the invention alternate reactants can be used for direct formation of methyl-esters including but not limited to boron trifloride in methanol, tetramethyl ammonium chloride and similar reagents commonly used for the trans-esterification of fatty acids.

In an embodiment of the invention, a triacyl-glyceride containing sample is combined with a methylating reagent in open air on a conducting screen which can be rapidly heated by application of an electric current to the screen. Rapid heating of the screen as inert carrier gas containing metastable helium atoms flow through the screen leads to desorption of the reaction products into the vapor phase where ionization occurs. The use of inert gas results in generation of protonated molecules of the fatty acid methyl esters. The reaction products can be detected in seconds using a mass spectrometer.

In an embodiment of the invention, determination of the type and percentage of fatty acids present in the original sample can be accomplished by measuring the relative ratios of each fatty acid methyl ester. This can typically be carried out by introducing isotopically labeled fatty acids to the original reaction mixture prior to heating and desorption ionization. While the relative ionization potential of individual fatty acid methyl esters may vary, the use of these standards will serve to provide correction coefficients for use in assigning the relative ratio of the fatty acids present in the mixture.

Thermal desorption of samples in the DART carrier gas stream can be carried out using a heated filament. This technique can produce ions characteristic of the analyte molecules present in the sample. As shown in FIG. 1, sample analysis can be completed by applying a small amount of sample onto a probe (102) with a filament at its distal end (128) and inserting the filament into the gap between the DART source (101) and the API-inlet of the mass spectrometer (152). A variable current power supply (160) can be used to heat the wire and desorb analyte molecules. The resulting mass spectrum contains the ions typically observed for the DART experiment however placing the filament in close proximity to the atmospheric pressure inlet resulted in a weak signal which was consistent with dramatically lowered and therefore unstable ion production. As unstable ion current can have a deleterious effect on both reproducibility and sensitivity the approach was inadequate for use in quantitative analysis and detection of trace contaminants which require stable background for signal processing.

In order to address the issue of instability caused by the electrical field in the desorption ionization region a large format mesh (216) inserted in a mesh holder (290) can be placed in the region between the DART source (201) and the API inlet of the mass spectrometer (252) and a gas ion separator used as an insulator/isolator (234). A gas ion separator is a device that can improve the signal to noise ratio of DART ionization. The gas ion separator can consist of a short length of tubing placed between the desorption ionization region at the distal end of the DART source and the API inlet of the spectrometer. The gas ion separator can be used to transportions to the API-inlet. However as it can also act in this experiment as an electrical insulator or isolator. In various embodiments of the invention shown in FIG. 2, a gas ion separator (234) can be positioned between the mesh (216) and the API-inlet of the mass spectrometer (252) resulting in increased ion production while not limiting the amount of carrier gas introduced into the spectrometer. The implementation of this experimental configuration diminished the instability by increasing the distance between the metal of the wire to which the sample was applied and the metal surface of the atmospheric pressure inlet (252), which often carries a high electric potential. The mass spectra acquired by using a direct probe inserted in the gap between the DART source and the API-inlet of the mass spectrometer can therefore be stabilized by using the gas ion separator (234).

The experimental configuration where the mesh is loaded with sample and placed between the DART source and API inlet of the mass spectrometer detector is referred to as the 'Transmission DART' mode. In various embodiments of the invention, the heated ionizing carrier gas flows through and across the mesh surface rather than around it. In various embodiments of the invention, Transmission DART promotes desorption ionization and detection of molecules with good sensitivity. The observation that ionization was possible at lower carrier gas temperature when using the mesh compared to desorption directly from a non-conducting surface as in conventional DART, i.e., with desorption from a glass capillary tube led to the design of a rapid heating system.

In various embodiments of the invention, shown schematically in FIG. 3 a heated carrier gas exits a DART source (301) and contacts a sample coated onto a mesh (316). The mesh (316) can be positioned between the source (301) and the proximal end of a gas ion separator (334) capable of transporting ions produced from that sample to the sampling region of an atmospheric pressure inlet of the mass spectrometer. Separate electrical leads from the positive and negative terminals of a variable current, low voltage power supply (360) can be connected to opposite sides of the wire grid in order to supply an electric current through the mesh.

Figure 4B:
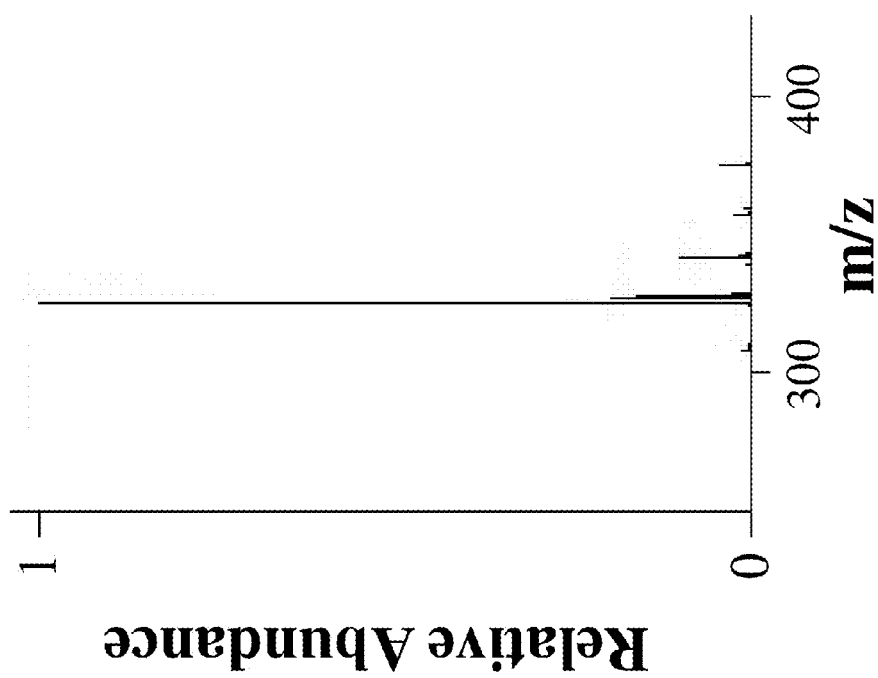

In various embodiments of the invention, positioning a sample stage comprised of a mesh placed in-line between the exit of the DART source and the API inlet of the spectrometer enables Thermally Assisted ionization of analytes using DART, (TA-DART). In various embodiments of the invention, using the DART source with room temperature carrier gas and passing approximately 1-7 Amps of current through the mesh resulted in the desorption ionization of molecules in a few seconds. The mass spectra measured were comparable to mass spectra obtained with the carrier gas increased to high temperatures (above 300 degrees Centigrade). The mass spectra measured with heated carrier gas required several minutes before the measurement could be undertaken. In various embodiments of the invention, using the DART source with room temperature carrier gas for analysis of an aliquot of quinine deposited on the mesh was completed in less than 25 seconds by rapidly raising the current passing through the mesh from approximately 0 Amps initially to approximately 6 Amps. The resulting mass chromatogram (FIG. 4(A)) shows a rapid desorption profile. FIG. 4(B) shows the mass spectrum of the $[M+H]^+$ ion region with little or no fragmentation or oxidation. Under conventional DART analyses conditions desorption of quinine requires a gas temperature of approximately 300 degrees Centigrade. The spectra from experiments carried out with TA-DART revealed similar sensitivity and signal intensity for molecules of interest detected as intact protonated molecules to those of the conventional DART experiment.

Figure 5A:
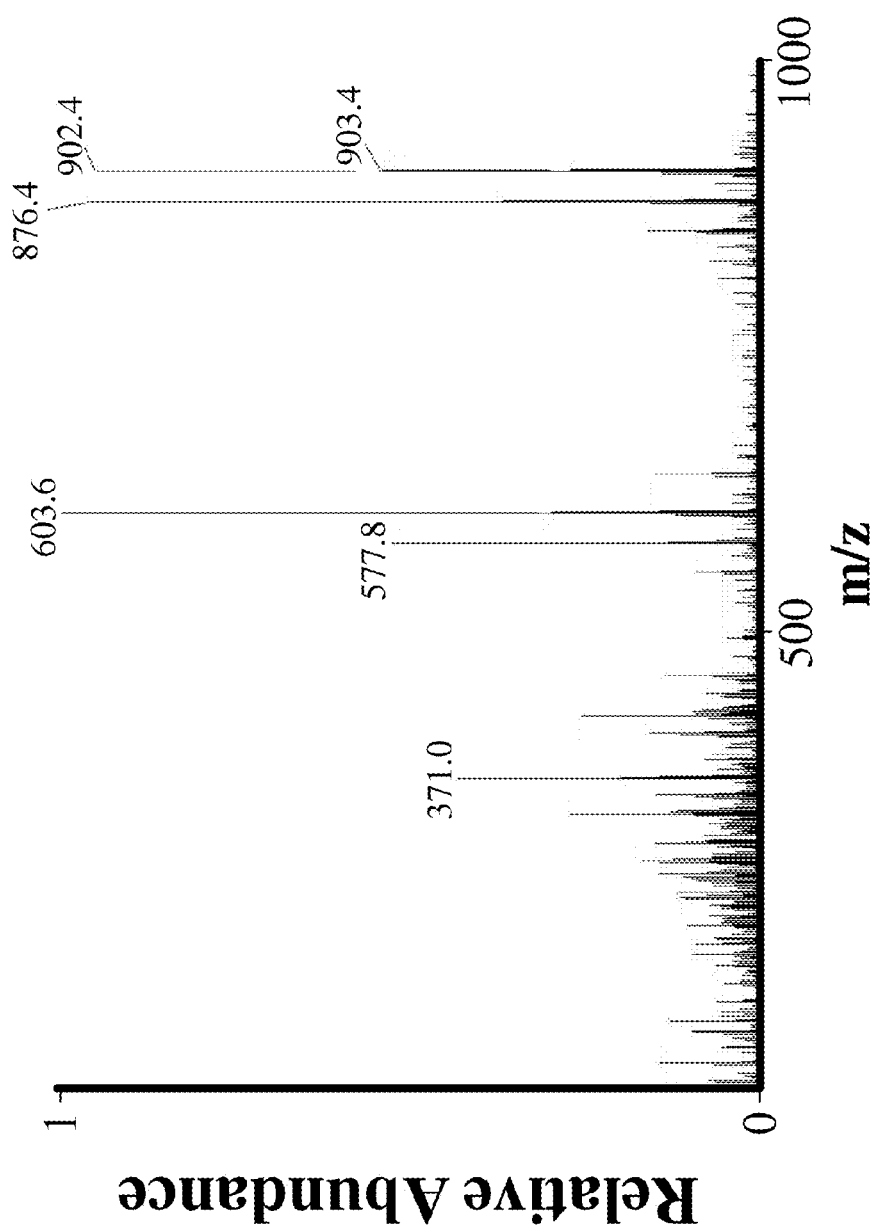
FIG. 5A is a mass spectrum of a sample of Extra Virgin Olive oil acquired using a thermal assisted DART source with carrier gas temperature of 50 degrees Centigrade and a current of approximately 4.5 Amps applied to the mesh according to an embodiment of the invention.
Figure 5B:
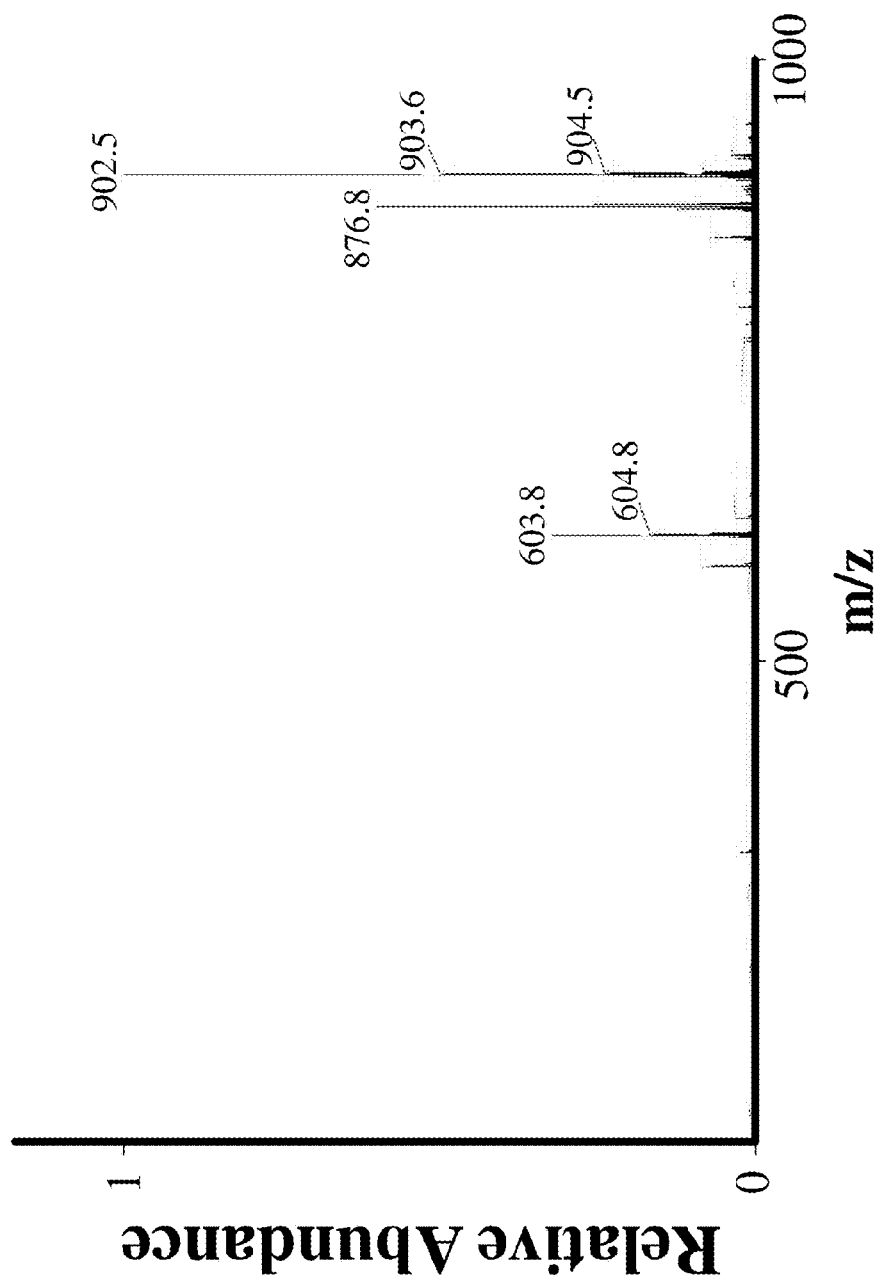
FIG. 5B is a mass spectrum of a sample of Extra Virgin Olive oil acquired using a thermal assisted DART source with carrier gas temperature of 50 degrees Centigrade and a current of approximately 6.5 Amps applied to the mesh according to an embodiment of the invention.

Olive Oil contains predominantly triglycerides with approximate mass of 900 Dalton. The TA-DART spectra for Olive Oil revealed an unexpected result compared with the conventional DART. The spectrum shown in FIG. 5A (with ions at m/z 371.0, 577.8, 603.6, 876.4, 902.4 and 903.4) is similar to conventional DART analysis of this type of oil, see for example Vaclavik, L., Cajka, T., Hrbek, V., Hajslova, J., Ambient mass spectrometry employing direct analysis in real time (DART) ion source for olive oil quality and authenticity assessment. Analytica Chimica Acta 645 (2009) 56-63, which article is herein explicitly incorporated by reference in its entirety. FIG. 5A was acquired as the current applied to the mesh was at an intermediate value of approximately 4.5 Amps. The presence of numerous ions in the mass range from 250-600 Dalton can be due to thermal degradation products of the intact triglycerides. However, as shown in FIG. 5B (with ions at m/z 603.8, 604.8 876.4, 902.5, 903.6 and 904.5) a significant decrease in low mass ions was observed in the TA-DART spectrum when an even higher current of approximately 6.5 Amps was applied to the mesh. For example, there was a reduction in relative abundance of diglyceride related ions in the 500-610 Dalton mass range and the absence of mono-glyceride related ions in the 250-400 Dalton mass range. The cleaner mass spectrum produced by using higher current TA-DART can be easier to interpret since the spectrum is dominated by the major intact ions. This result was consistently observed even when very high currents were used to generate temperatures on the wire surface significantly higher than temperature normally achieved in conventional DART with a heated carrier gas.

In various embodiments of the invention, TA-DART generates protonated intact molecules that would normally require a DART carrier gas temperature in excess of approximately 400 degrees Centigrade. In various embodiments of the invention, TA-DART can be used to measure a spectrum of a sample in approximately ½oth of the time required to measure a spectrum of a sample with Conventional DART using carrier gas heated to a temperature of approximately 400 degrees Centigrade. In various embodiments of the invention, TA-DART results in a significant reduction in the production of ions derived from thermal degradation. In various embodiments of the invention, TA-DART can enable a wider field of use of DART.

Reducing thermal decomposition of triglycerides has a practical application in the direct analysis of blood for chemicals of interest. DART analysis of blood plasma and whole blood spots for pharmacological studies have produced abundant low mass ions which limited the utility of the method, see for example Zhao Y., L. M., Wu D., Mak R., Quantification of small molecules in plasma with direct analysis in real time tandem mass spectrometry, without sample preparation and liquid chromatographic separation. Rapid Communications in Mass Spectrometry, 2008, 22(20): p. 3217-3224 and Yu, S., et al., Bioanalysis without Sample Cleanup or Chromatography: The Evaluation and Initial Implementation of Direct Analysis in Real Time Ionization Mass Spectrometry for the Quantification of Drugs in Biological Matrixes. Analytical Chemistry, 2008. Anal. Chem. 2009, 81, 193-202, both articles are herein explicitly incorporated by reference in there entireties.

Since the mass of many drug candidates is in the same mass region as the products of lipid decomposition a reduction in generation of those products would be especially desirable. The potential that TA-DART might produce a simpler mass spectrum from human and animal blood which contains triglycerides with greater fatty acid diversity as well as significant concentration of phosphatidyl-ethanol amines, phosphatidyl-cholines, phosphatidyl-serines and phosphatidyl-inositols can enable lower detection limits for drug components.

A comparison of the mass spectra from whole blood by conventional DART and TA-DART confirmed the utility of the TA-DART method for detection of drugs in blood. The absence of major ions in the low mass range with TA-DART suggest that many drugs in that mass range can be more easily detected with greater signal-to-noise.

Figure 6:
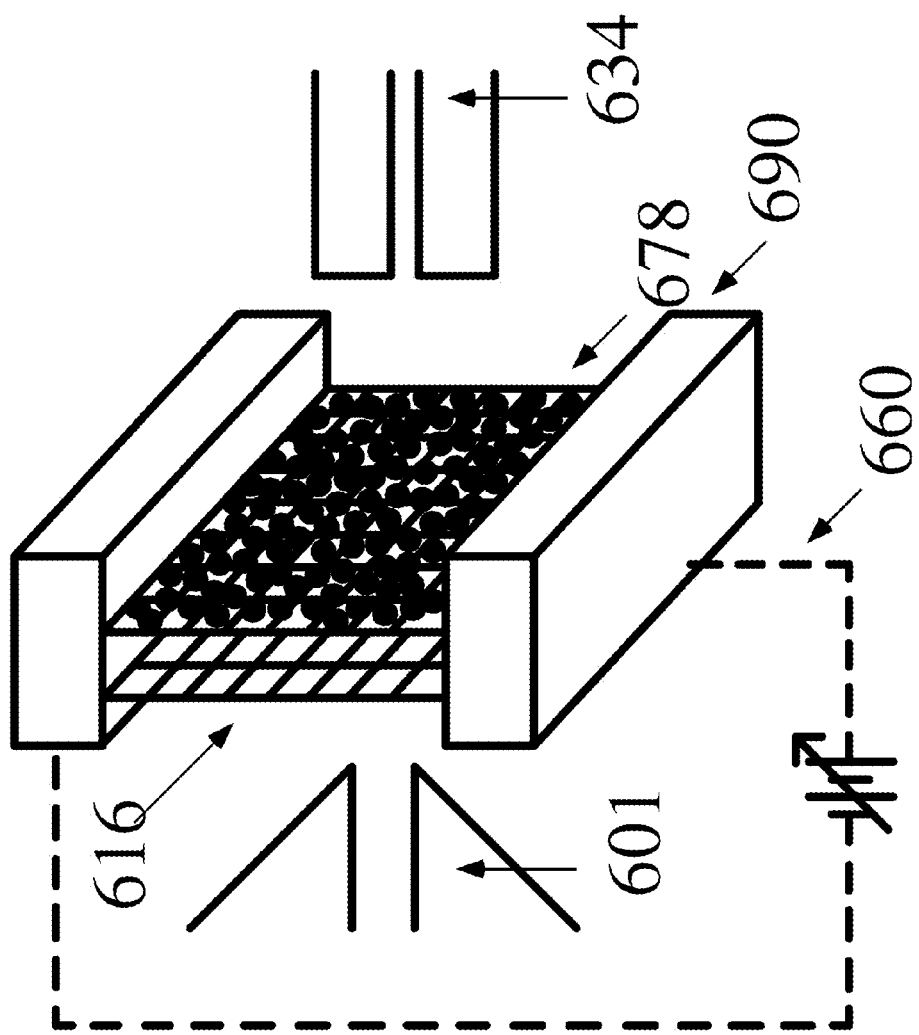
FIG. 6 is a schematic diagram of a sampling system incorporating an ionizing gas source, a mesh with a porous material applied to the mesh, a power supply to heat the mesh according to an embodiment of the invention.

Another class of thermally sensitive molecules includes pesticides. Fruit can be sampled by rubbing the fruit on a piece of polyethylene foam material. After sample collection, the piece of foam was positioned between the conventional DART source and entry tube of the gas ion separator attached to the API-MS. Heating the DART carrier gas from approximately 150° C.-400° C. required 2 minutes during which time the pesticides collected on the foam were ionized and transferred to the mass spectrometer for detection. The pesticides were desorbed over very long periods of time making quantitation difficult. The thermal properties of the foam, unlike the mesh, increased the time needed to reach the maximum temperature. Placing a mesh in close proximity to the foam can allow a more rapid heating of the foam thus facilitating more rapid analysis. FIG. 6 shows a schematic diagram of a sampling system incorporating a mesh (616) inserted in a holder (690) positioned between the ionizing gas source (601) and porous material (678) upon which the sample to be analyzed is applied, where the porous material (678) is positioned in close proximity to a gas ion separator (634) which permits transfer of ions to the API-inlet of the mass spectrometer according to various embodiments of the invention. A power supply (660) is used to heat the mesh.

Figure 10:
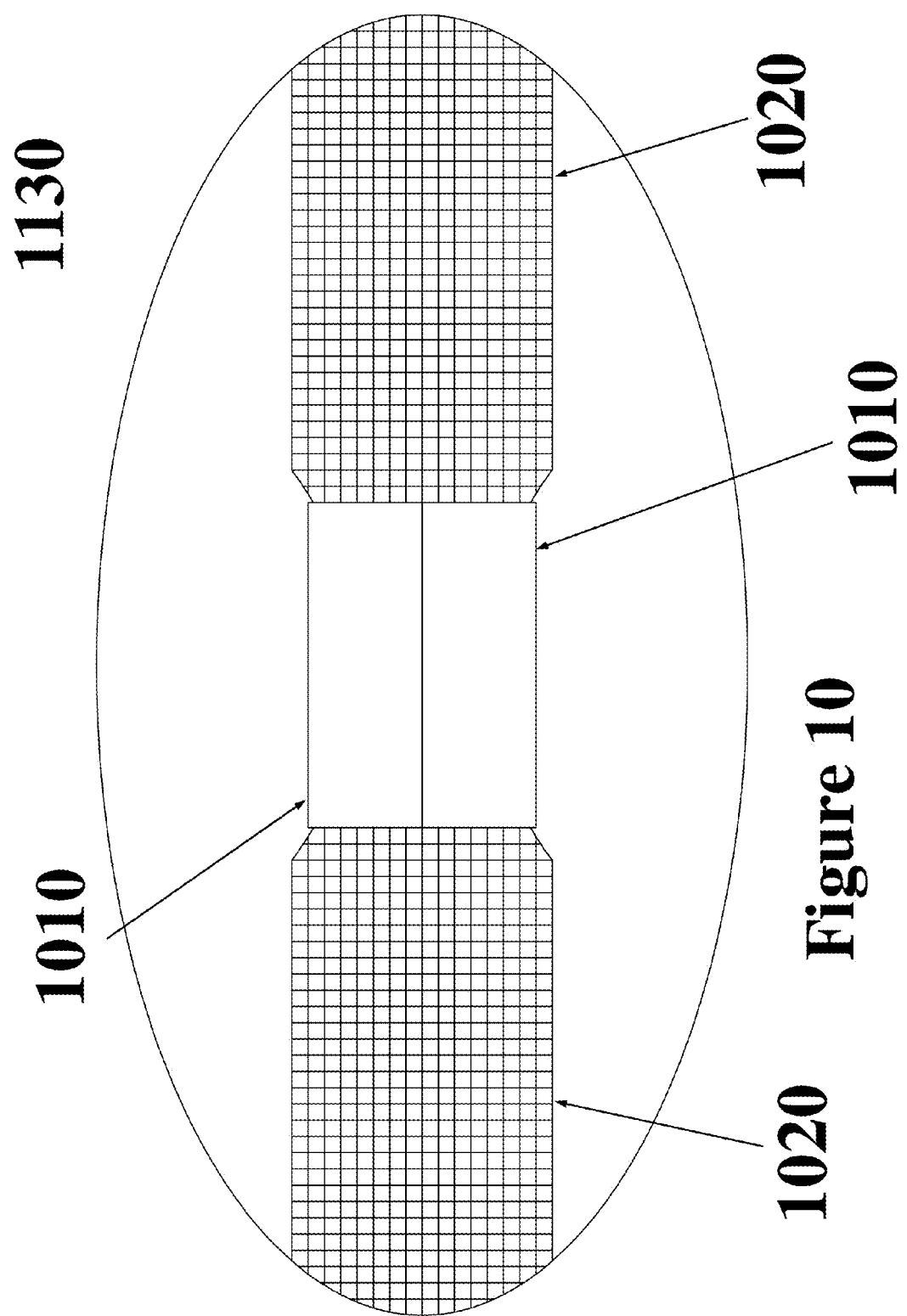
FIG. 10 shows a drawing of a foam sponge plastic attached to a mesh, according to an embodiment of the invention.
Figure 11:
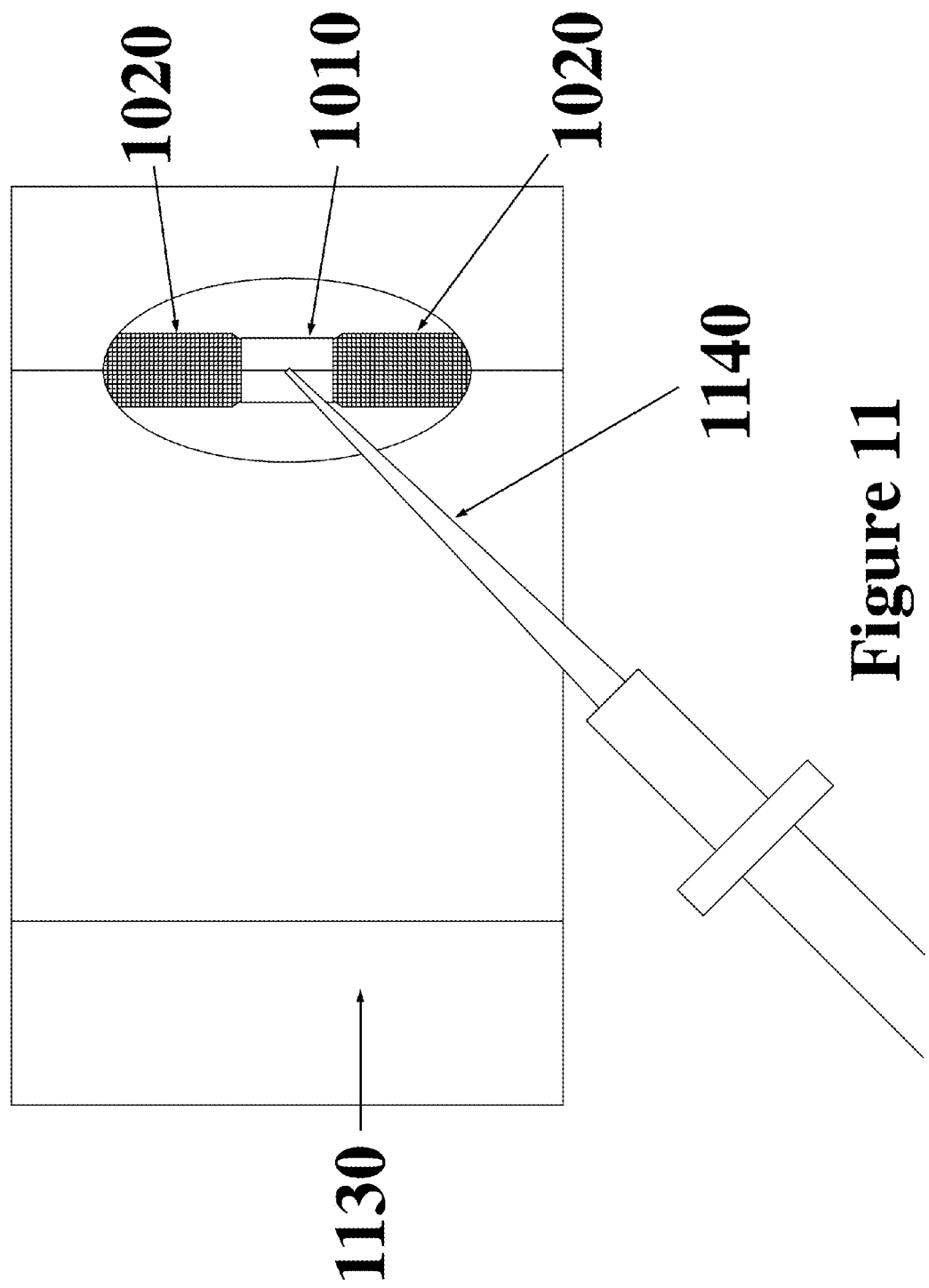
FIG. 11 shows a drawing of the liquid sample being applied to a foam sponge plastic attached to a mesh associated with a card, according to an embodiment of the invention.
Figure 13:
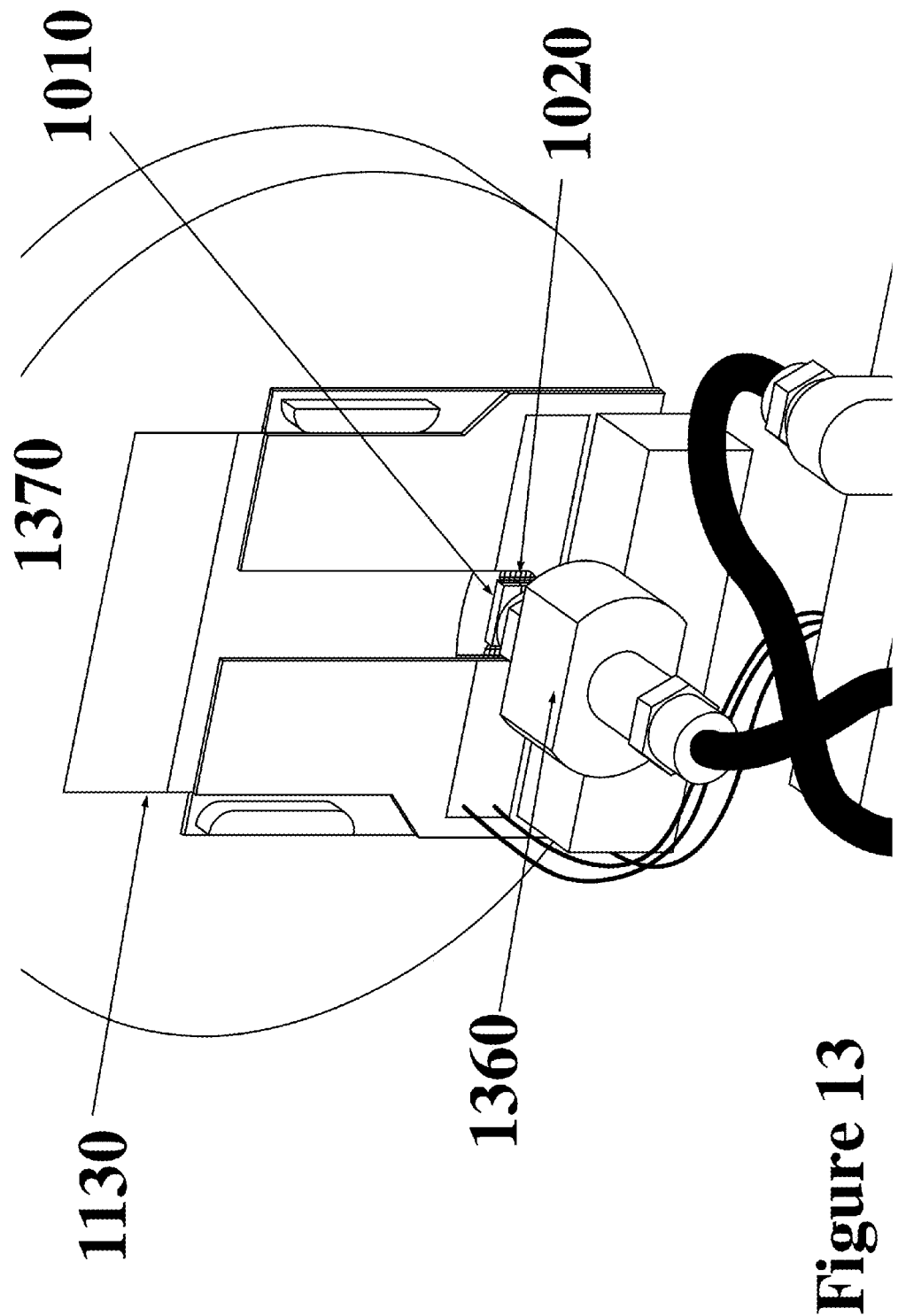
FIG. 13 shows a drawing of the foam sponge plastic attached to a mesh associated with a card which can be heated by a power supply, wherein the foam sponge plastic and the mesh are positioned between the ionizing gas source and a gas ion separator, according to an embodiment of the invention.

In various embodiments of the invention, the foam sponge plastic 1010 shown attached to the wire mesh 1020 applied to a card holder in FIG. 10 can be used to contain a solid, liquid or gas/liquid sample. As shown in FIG. 11, a liquid sample can be deposited from a pipette 1140 onto the foam sponge plastic 1010 shown attached to the wire mesh 1020 associated with a card holder 1130. FIG. 13 shows a foam sponge plastic 1010 attached to a mesh 1020 associated with a card 1130 mounted on the entrance to a mass spectrometer 1370 positioned between the ionizing gas source 1360 and a gas ion separator (not shown) which permits transfer of ions to the API-inlet region of a mass spectrometer (not shown). FIG. 14 shows (A) a total ion chromatogram (TIC) over the time interval zero to two minutes obtained using a carrier gas temperature of 50 degrees Centigrade while rapidly increasing the current passing through the mesh supporting the sample applied to a foam sponge plastic from 0 Amps at time=0, to 6 Amps at time=30 second; (B) a partial mass chromatogram of the 195 Dalton ion produced during the two minute analysis shown in FIG. 14A; and (C) the mass spectrum (including ions at m/z 217.0 and 233.9) obtained by summing the spectra obtained between 0.68-1.08 minutes of the TIC shown in FIG. 14A.

In various embodiments of the invention, a non-conducting porous material is placed between a pair of mesh strips to hold the non-conducting material positioned immediately between the DART source and the API inlet. The current to the mesh can be gradually increased in order to both implement a source of radiant heat near the non-conducting material (foam) and increase the gas temperature as it passed through the mesh.

Figure 7:
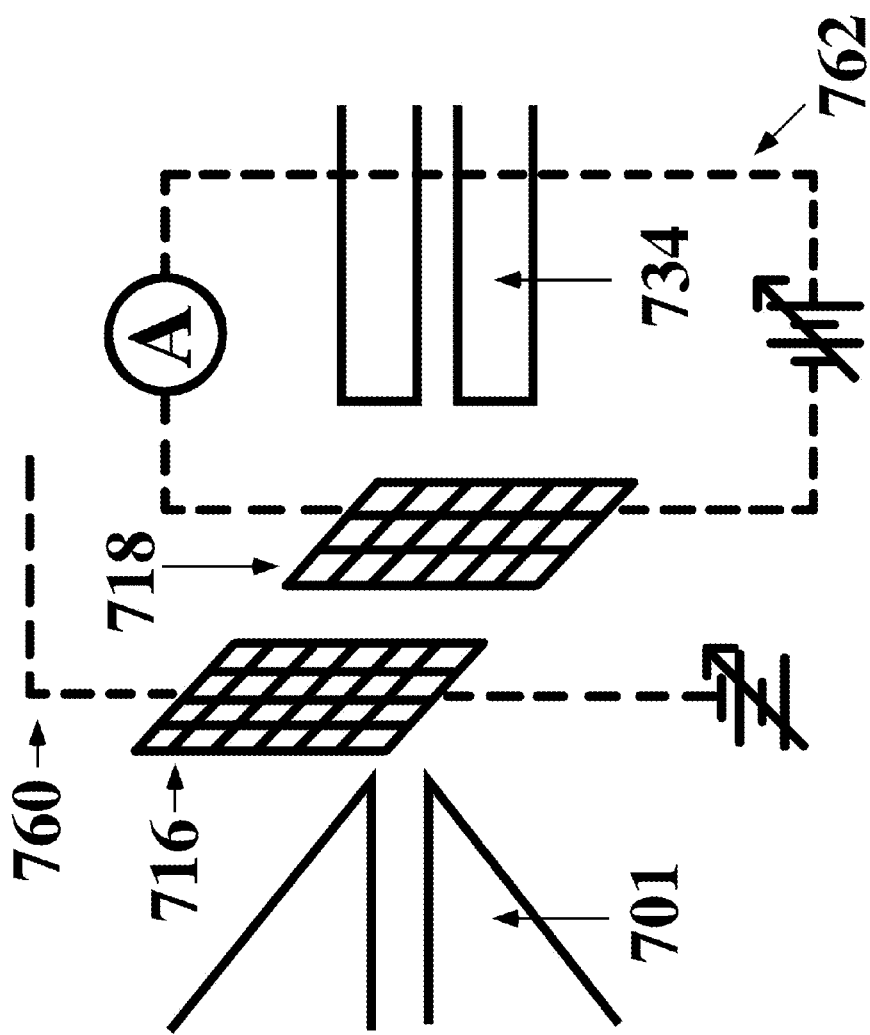
FIG. 7 is a schematic diagram of a sampling system incorporating an ionizing gas source with two mesh pieces with independent power supplies, wherein the meshes are positioned between the ionizing gas source and the sample to be analyzed where the sample is positioned in close proximity to a gas ion separator which permits transfer of ions to the API-inlet region of the mass spectrometer according to an embodiment of the invention.

FIG. 7 shows a schematic diagram of a sampling system incorporating two meshes (716, 718) with two power supplies (760, 762, only a portion of the 760 circuit is shown), wherein the meshes (716, 718) are positioned between the ionizing gas source (701) and the sample to be analyzed, where the sample is positioned in close proximity to a gas ion separator (734) which permits transfer of ions to the API-inlet region of the mass spectrometer according to various embodiments of the invention.

FIG. 8 shows a schematic diagram of a sampling system incorporating two meshes (816) with a single power supply (860), wherein the meshes (816) are positioned between the ionizing gas source (801) and the sample to be analyzed, where the sample is positioned in close proximity to a gas ion separator (834) which permits transfer of ions to the API-inlet region of the mass spectrometer according to various embodiments of the invention. A variable resistor (872) is used to apply different currents to the two different meshes. The device shown in FIG. 8 enables the passage of different currents through two or more different meshes in order to differentially desorb samples from the two or more different meshes (816). In various embodiments of the invention, the device shown in FIG. 8 can be used to generate dopant gas to promote ionization of sample molecules. In various embodiments of the invention, the device shown in FIG. 8 can be used to vaporize a reference molecule independent of the sample molecule in order to facilitate accurate mass measurement. In various embodiments of the invention, the device shown in FIG. 8 can be used to vaporize a reference molecule independent of the sample molecule in order to perform quantitation of the sample molecule. The variable resistor 872 can be used to adjust the current thus permitting more accurate adjustment of the temperature applied to the second mesh. In various embodiments of the invention, the device shown in FIG. 8 can be used to vaporize a reference molecule independent of the sample molecule in order to determine a correlation between current applied and temperature on the mesh so that the current applied to the second mesh can be adjusted to a specific temperature.

Figure 15:
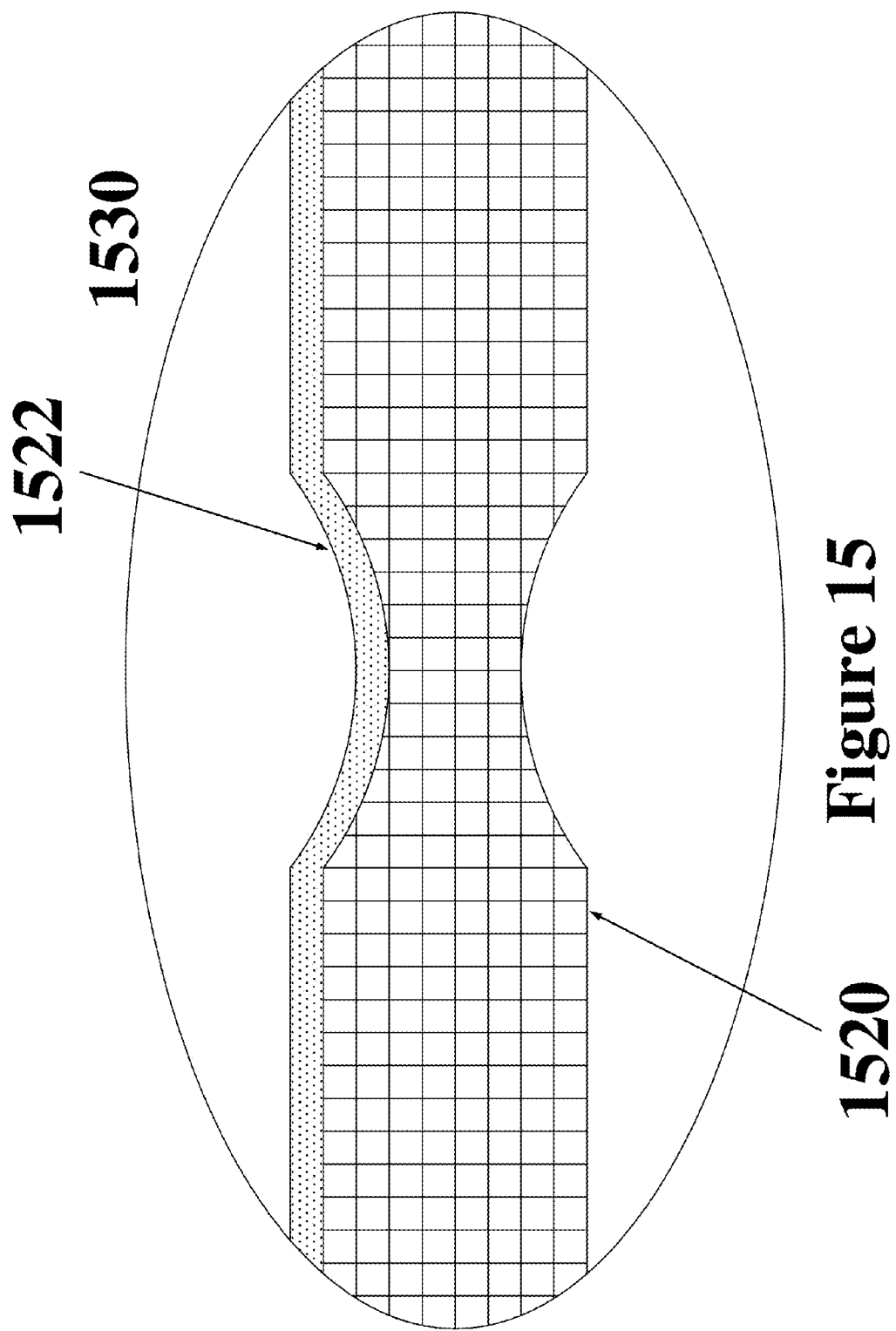
FIG. 15 shows a drawing of the two mesh associated with a card, according to an embodiment of the invention.
Figure 18:
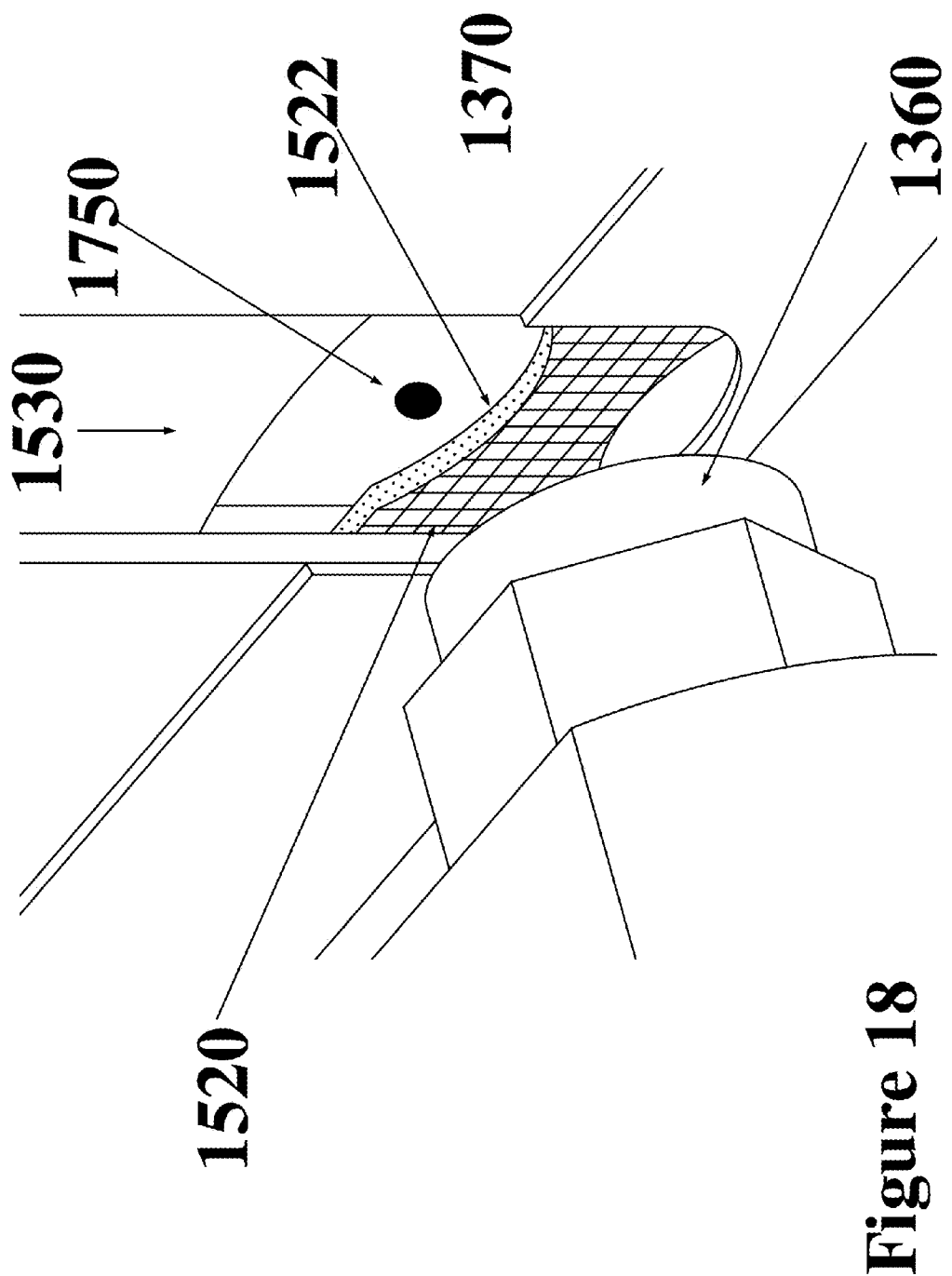
FIG. 18 shows a drawing of the two mesh associated with a card positioned in close proximity to the API-inlet region of a mass spectrometer, according to an embodiment of the invention.
Figure 19:
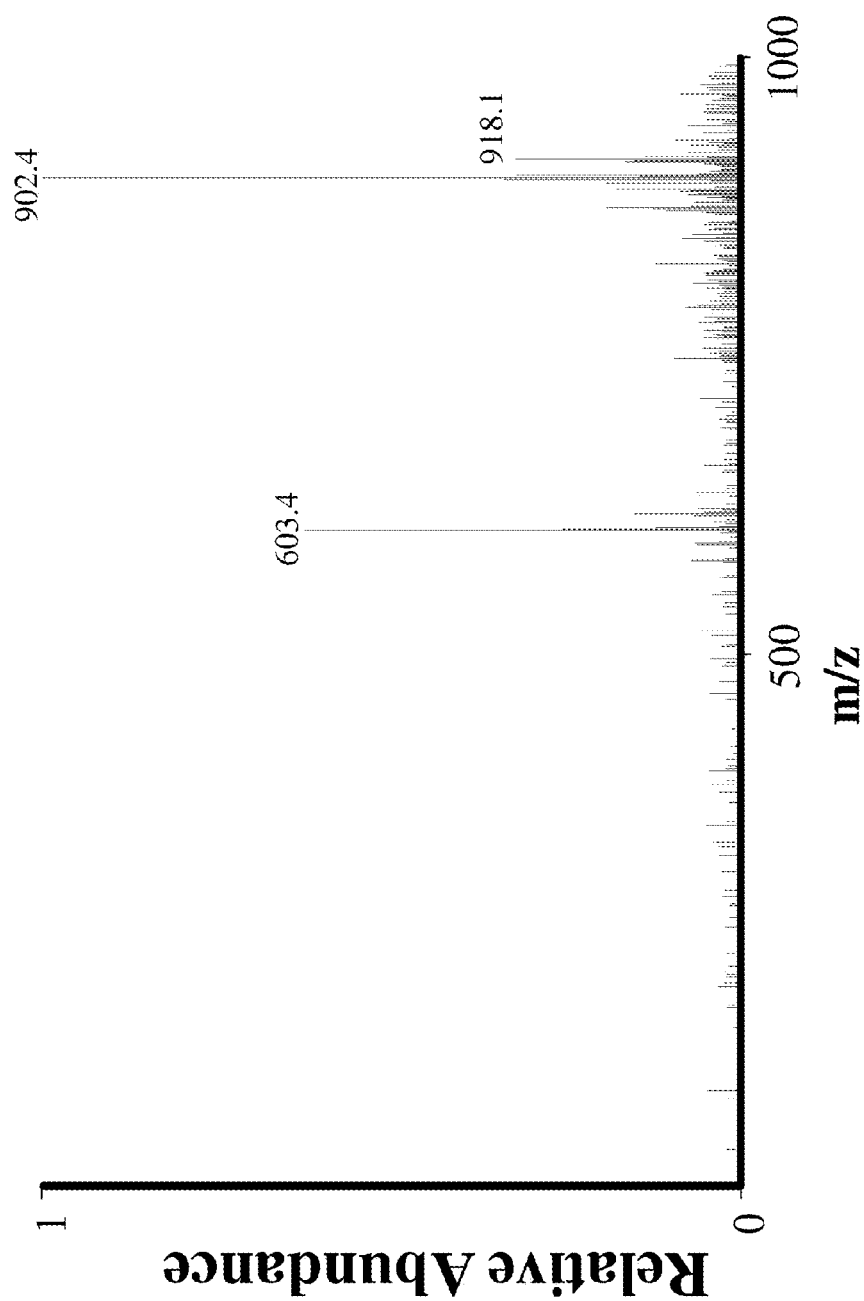
FIG. 19 shows the mass spectrum obtained from a sample of olive oil in toluene applied to a mesh and ammonia applied to second mesh, wherein both mesh are associated with a card which was heated by a single power supply (not shown), according to an embodiment of the invention.
Figure 20:
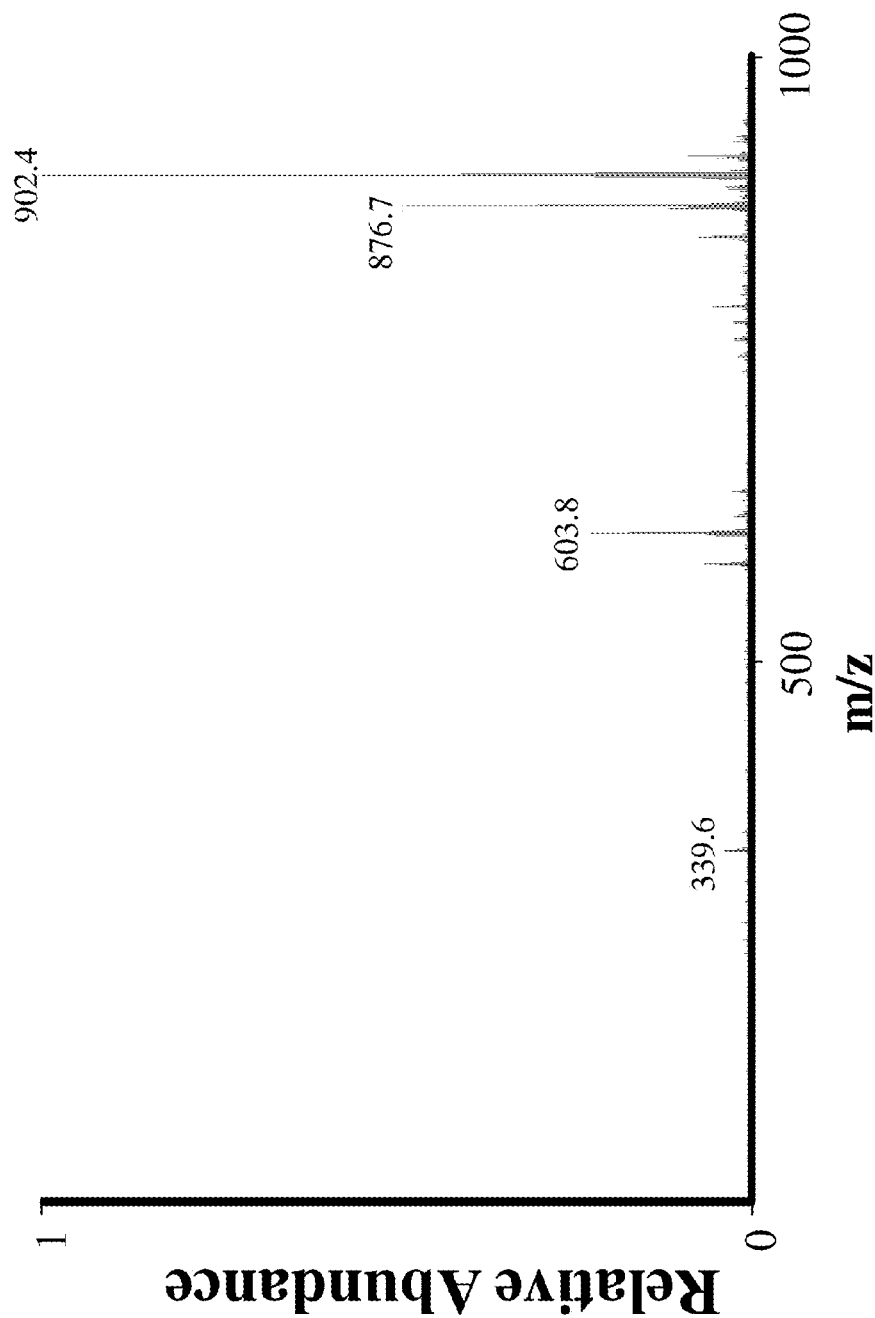
FIG. 20 shows the mass spectrum obtained from a sample of olive oil in toluene applied to a mesh associated with a card which was heated by a power supply.

In various embodiments of the invention, two wire mesh 1520 and 1522 associated with a card 1530 as shown in FIG. 15 can be heated by a single power supply (not shown) and used to analyze a sample. FIG. 18 shows (the side perspective) of the two mesh 1520 and 1522 associated with a card 1530 from FIG. 15 mounted on the entrance to a mass spectrometer 1370, between the distal end of the ionizing source 1360 and the API-inlet region 1750. FIG. 19 shows the mass spectrum (with ions at m/z 603.4, 902.4 and 918.1) obtained from a sample of a solution containing 1% olive oil dissolved in toluene an aliquot of which is applied to the first mesh placed between the distal end of the ionizing source and a second mesh to which a solution of ammonia was applied, wherein both mesh are associated with a card configured to permit heating by a single power supply. For comparison, FIG. 20 shows the mass spectrum (with ions at m/z 339.6, 603.8, 876.7 and 902.4) obtained from analysis of an aliquot of olive oil dissolved in toluene applied to a single mesh associated with a card which was heated by a power supply. The use of ammonia as a dopant (see FIG. 19) increased the formation of the ammonia adduct of the triglycerides while decreasing the abundance of the protonated molecules (not intense) (see FIG. 20).

FIG. 9A shows a schematic diagram of a sampling system incorporating a card (999) with a cut out region (998), and a reservoir (994) wherein one or more tubes (990, 992, 996) are associated with the reservoir (994) and the card (999) is positioned between an ionizing gas source (901) and a gas ion separator (934) which permits transfer of ions to the API-inlet region of the mass spectrometer according to various embodiments of the invention. In various embodiments of the invention, a sample can be introduced into the reservoir (994) through one or more tubes (990, 992) to allow for liquid analysis transmission mode DART. In various embodiments of the invention, a filament or a mesh (not shown) can be positioned associated with the card (999) at the cut our region (998). In alternative embodiments of the invention, no filament or mesh is associated with the cut our region (998) and the gaseous sample interacts with the ionizing species in the cut out region (998). A sample in the reservoir (994) can be introduced into the cut out region (998) through a tube (996). In various embodiments of the invention, the device shown in FIG. 9A can be used to introduce a solid, liquid or gaseous sample from the reservoir (994) for desorption and ionization. In various embodiments of the invention, the device shown in FIG. 9A can be used to continuously introduce a liquid sample for desorption and ionization. In embodiments of the invention, a filament positioned in the cut out region (998) can be used to create a potential difference between a conducting tube (996) to electrospray the sample into the cut out region (998). In various embodiments of the invention, the device shown in FIG. 9A can be used to apply a current at regular intervals to a mesh associated with the cut out region (998) to enable the periodic desorption of introduced liquid or gaseous samples. In various embodiments of the invention, in the device shown in FIG. 9A, the tube (990) can be coupled to a liquid chromatography system for desorption and ionization of the analytes eluted off the chromatographic material (994). In alternative embodiments of the invention, the chromatography can be accomplished prior to introduction of the stream onto the card and the volume of the reservoir minimized to the volume of the tubing (990, 992, 996).

Figure 9D:
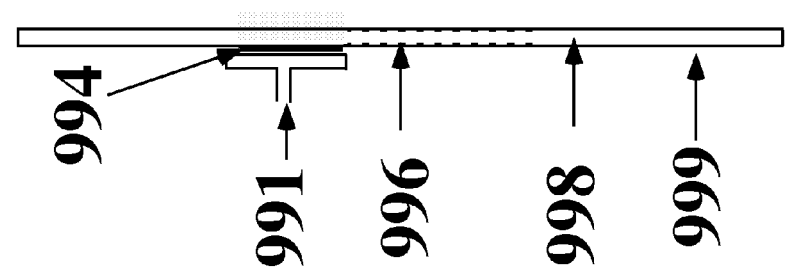
Figure 9C:
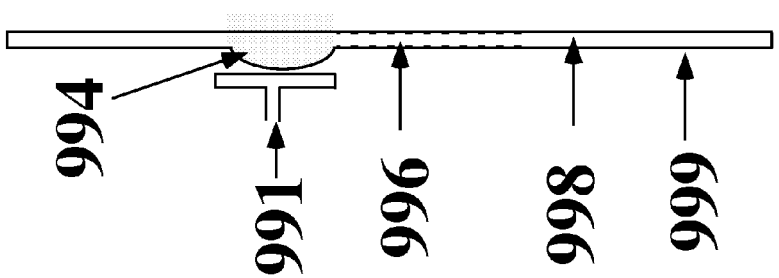
Figure 9B:
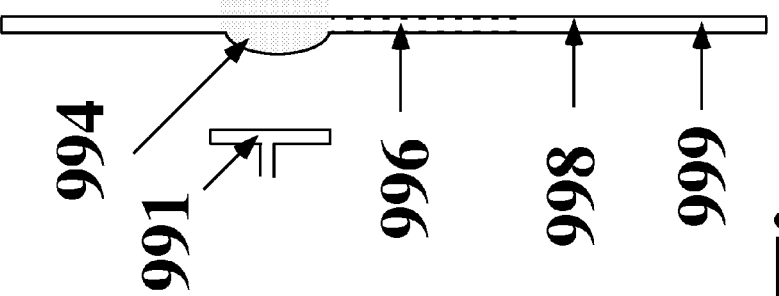

In various embodiments of the invention, the reservoir shown in FIG. 9A can be depressed by the application of a trigger (991) to the reservoir (994) as shown in FIGS. 9B-9D. In various embodiments of the invention, by sealing or using a one way valve to stop flow through the introduction tube (see 990, 992 in FIG. 9A), the trigger (991) applies pressure to a flexible reservoir which dispenses the solution or vapor through tube (996) into the cut out region (998) of the card (999) (see FIGS. 9B-9D). The flexible reservoir can be made of rubber or a variety of plastics with sufficient elasticity to allow perturbation to deliver the solution or vapor. In various embodiments of the invention, the flexible reservoir can allow reloading of a sample after the solution or vapor has been delivered. In another embodiment of the invention, the reservoir is static and relies upon the application of electric fields or electro hydrodynamic pressure to deliver a solution through the tube (996).

In various embodiments of the invention, a series of different mesh strips through which different currents can be directed permits collection of multiple mass spectra from the same sample at different temperatures. This configuration can be desirable in order to avoid heating the sample too rapidly resulting in the rapid desorption of low mass, or more volatile molecules.

In various embodiments of the invention increasing the density of the mesh positioned between the source and proximal end of the gas ion separator results in a reduction in the number of ions related to the atmosphere surrounding the sample being detected. Analysis of samples with mesh positioned between the source and API-inlet also decreases the abundance of ions from the ambient air which normally contributes significant background to the mass spectrum. The reduction in background relative to production of sample related ions improves the signal-to-noise resulting in an increase in the sensitivity of the DART technique when using the mesh as a sample containment device.

In various embodiments of the invention, a mesh includes two or more components in physical contact selected from the group consisting of two or more connected wires or two or more connected strings, foam, polymers, silica, cellulose, and hydrophobic support material. In various embodiments of the invention, a mesh includes two or more components physically bound together selected from the group consisting of two or more connected wires or two or more connected strings, foam, polymers, silica, cellulose, and hydrophobic support material.

In various embodiments of the invention, a mesh can be contacted with the analyte and can then be analyzed. In various embodiments of the invention, a mesh can be in the spatial vicinity of the analyte, the mesh can be heated and the analyte analyzed.

In various embodiments of the invention, the heating of the mesh can be effected through the use of an infra-red (IR) laser. In various embodiments of the invention, the heating of the mesh can be accomplished by directing an IR laser onto specific sites on a mesh. The IR laser frequency can be absorbed by water molecules and the energy converted into heat to effect the desorption of the analyte.

In various embodiments of the invention, the heating or cooling of the mesh can be affected through the conductive transfer of heat from a heat sink. The temperature of the heat sink can be adjusted by transfer of electric current to the heat sink. The temperature of the heat sink which is located in the vicinity of the analyte applied to the mesh can then be used to adjust the temperature of the analyte.

In various embodiments of the invention, the heating of the mesh can be affected when in proximity to a radiant heat source such as a filament with an electric current passing through the filament.

Figure 12:
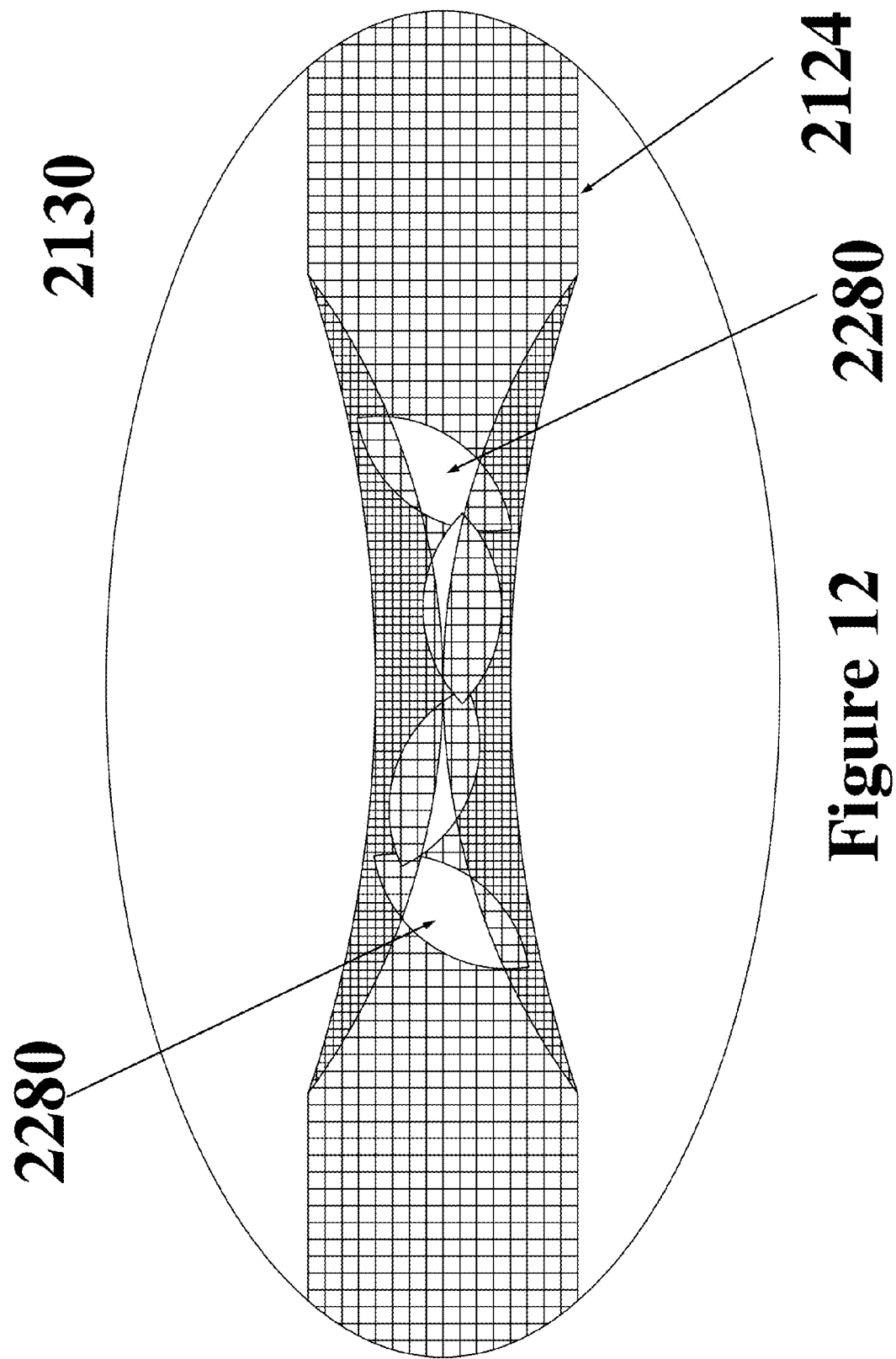
FIG. 12 shows a drawing of Oolong tea leaves enclosed in the mesh trough associated with a card, according to an embodiment of the invention.
Figure 16:
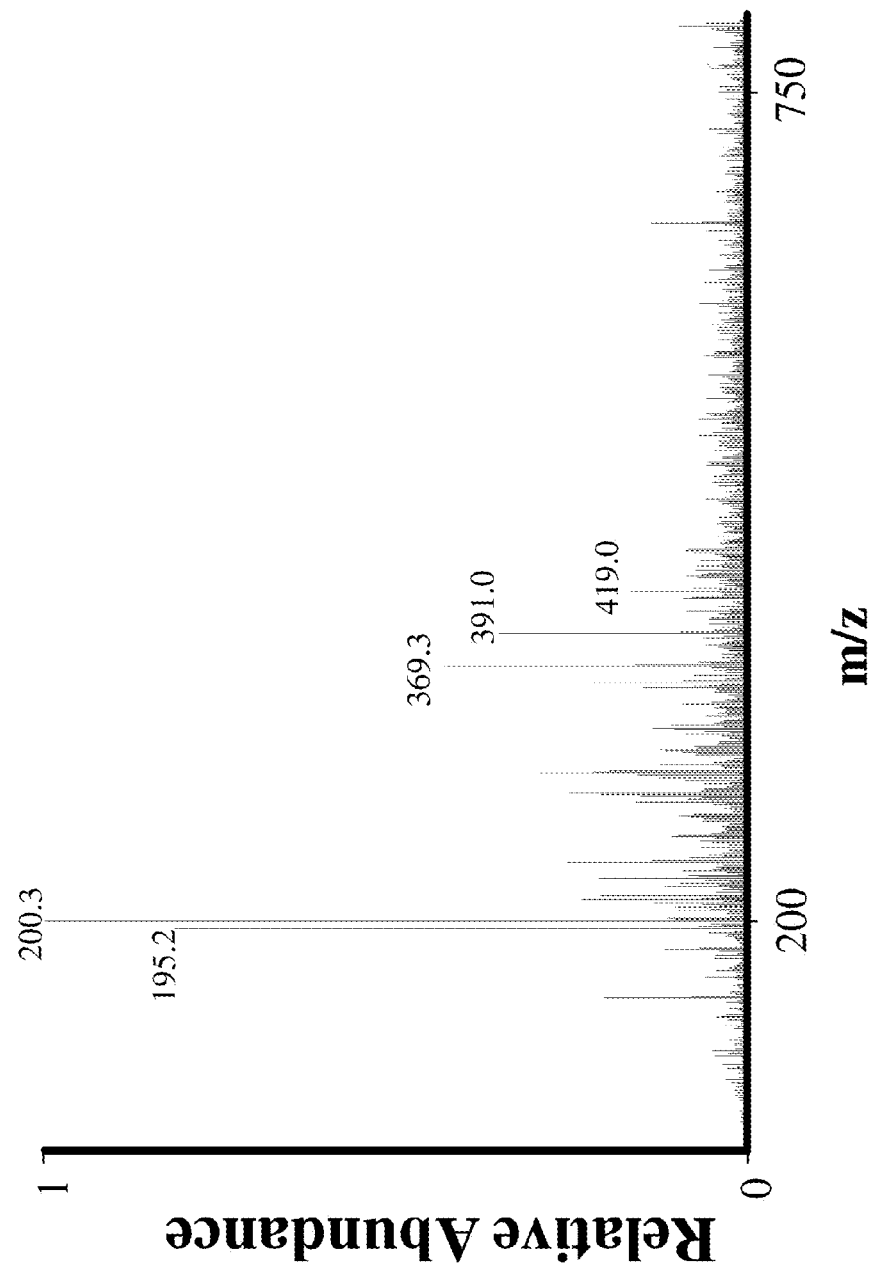
FIG. 16 shows the mass spectrum obtained from a sample of Oolong tea leaves enclosed in a mesh trough associated with a card which was heated by a power supply according to an embodiment of the invention.
Figure 17:
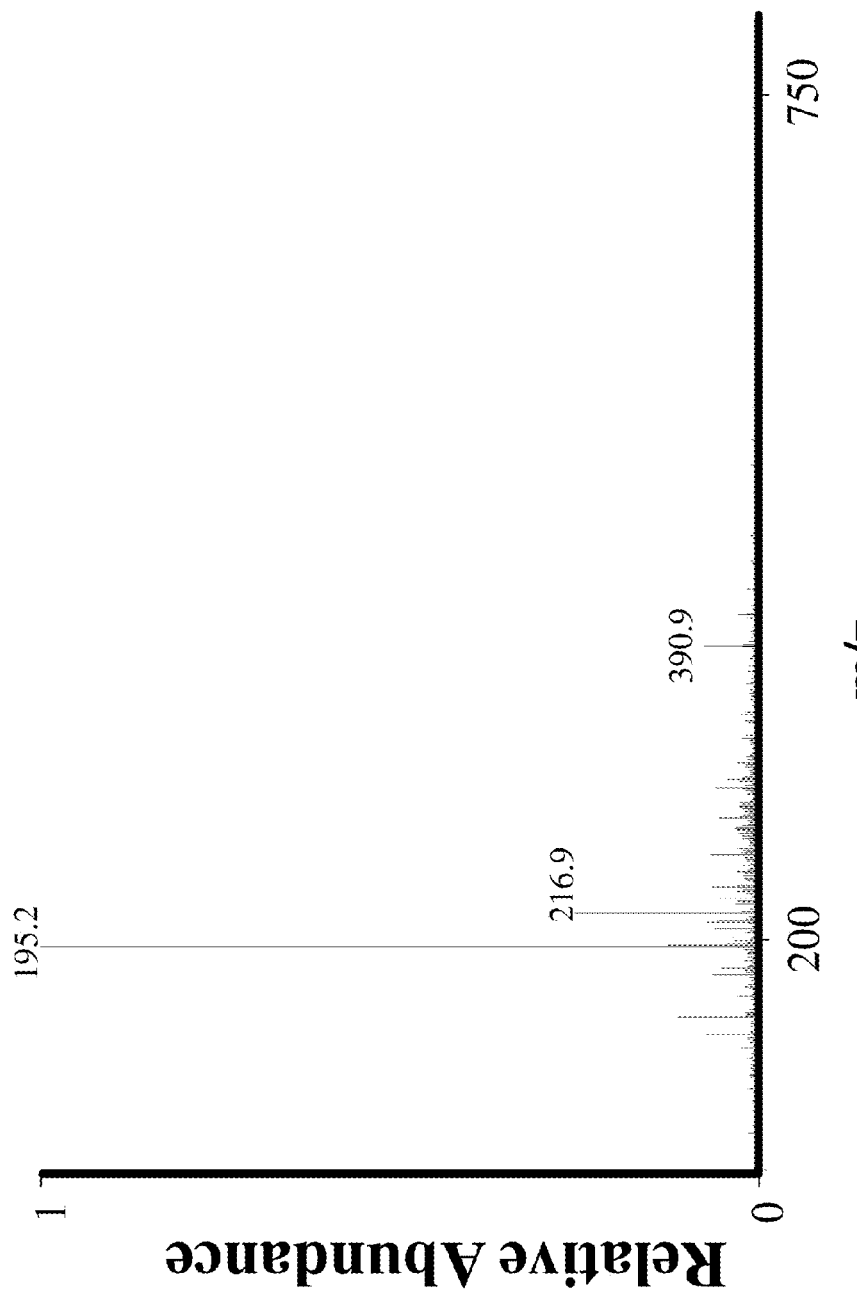
FIG. 17 shows a conventional DART mass spectrum obtained from a sample of Oolong tea leaves.
Figure 21:
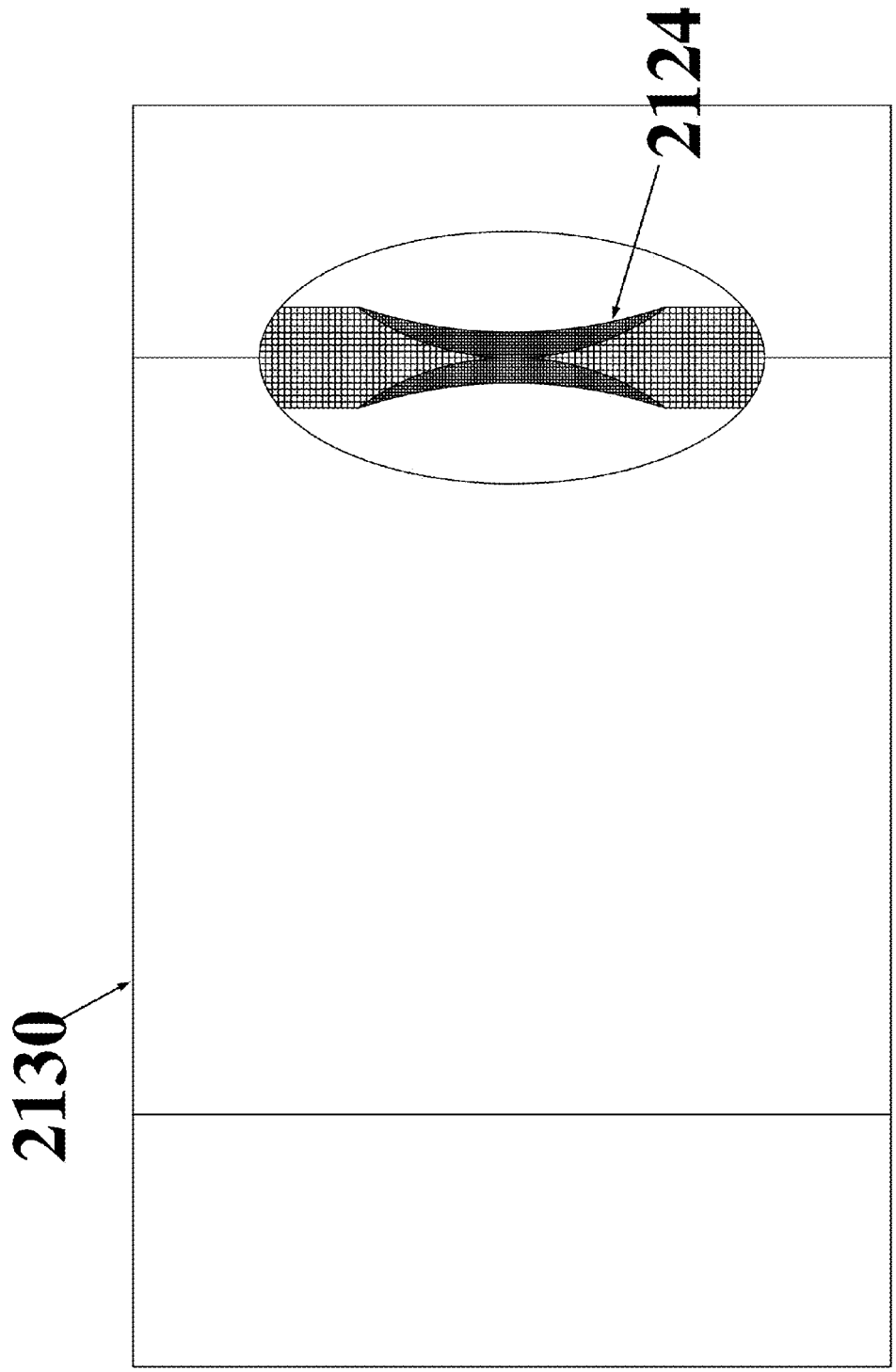
FIG. 21 shows a drawing of the mesh trough associated with a card, according to an embodiment of the invention.

In various embodiments of the invention, heating the mesh may be used to facilitate reactions of one or more analyte, the products of which reactions can be analyzed and can be used to infer the actual identity or quantity of the one or more analytes. In various embodiments of the invention, the mesh can be mounted on a card which can be used to isolate the analyte from contaminants, facilitating handling of the sample. In various embodiments of the invention, the material of the card is capable of absorbing or otherwise retaining and releasing a chemical to be used as a dopant to assist ionization at room temperature or after application of heat to vaporize the analyte or product. In various embodiments of the invention, the mesh is in the shape of a cylinder or tube of variable diameter and size, wherein liquid or solid sample is placed into the cylinder or tube through an opening. In various embodiments of the invention, the mesh is shaped like a "bowtie," with a thin spot in the middle and two ends that increase in width as they extend outward away from the center. In various embodiments of the invention, the mesh is in the shape of a "trough," with mesh for the bottom and two sides and an opening in the top with which to hold loose chemicals, leaves, pulverized materials, soil, cells, or solid particles for analysis. In various embodiments of the invention, a mesh trough 2124 associated with a card 2130 can be heated by a single power supply (not shown) and used to analyze a sample (see FIG. 21). FIG. 12 shows Oolong tea leaves 2280 held in a mesh trough 2124 associated with a card 2130 which can be heated by a power supply (not shown) according to an embodiment of the invention. FIG. 16 shows the mass spectrum (with ions at m/z 195.2, 200.3, 369.3, 391.0 and 419.0) obtained from a sample of Oolong tea leaves enclosed in a mesh trough associated with a card which was heated by a power supply according to an embodiment of the invention. FIG. 17 shows a conventional DART mass spectrum (with ions at m/z 195.2, 216.9 and 390.9) obtained from a sample of Oolong tea leaves. Comparison of the results generated by using the two approaches shows an increase the number and abundance of ions representative of the sample that have been generated using the greater sampling capacity of the mesh trough.

In various embodiments of the invention, a filament can be deployed with a card. In various embodiments of the invention, a mesh can be deployed with a card. By deploying the mesh with a card, the card can be held by the user while a sample can be applied to the mesh without the sample or the mesh being contaminated by the user.

In various embodiments of the invention, a reservoir capable of holding a gas or liquid can be deployed with a card. In various embodiments of the invention, a reservoir capable of holding a gas or liquid can be deployed in the vicinity of a mesh with a card. One or more tubes can be associated with the reservoir. One of the one or more tubes can be used for filling the reservoir with a liquid or gas sample. One or more tubes can be orientated towards a mesh. The reservoir can be filed or partially filed with a gas or solvent prior to insertion of the card into an instrument for analysis. The liquid or gas in the reservoir can be partially or fully expelled by the action of a force on the reservoir through the one or more tubes. The one or more tubes which can expel the liquid or gas can include a tube upon which an electrical potential can be applied to the tube. Applying the electrical potential to the tube can induce the liquid or gas to exit the reservoir. The tube exiting the reservoir can be orientated towards a mesh or a filament.

A device for analyzing an analyte comprising a spectrometer including an entrance for analyzing the analyte and a source including a proximal end and a distal end configured for generating ionizing species, where the distal end is proximal to the spectrometer entrance, where an atmospheric pressure region is located between the distal end of the source and the spectrometer entrance. The device further comprising a supply adapted to one or more of generate, transfer, conduct and radiate heat and one or more mesh positioned in the atmospheric pressure region, where the analyte is applied on or near the one or more mesh, where the supply can one or more of generate, transfer, conduct and radiate heat to the analyte, where analyte molecules desorbed from the one or more mesh interact with the ionizing species generated by the source to form a plurality of analyte ions which enter the spectrometer.

A device for analyzing an analyte which comprises a spectrometer including a proximal end and a distal end configured for analyzing the analyte, where an entrance for the analyte is located at the proximal end and a detector is located at the distal end, where an atmospheric pressure region is maintained through the length of the spectrometer between the proximal end and the distal end. The device further comprising a source including a proximal end and a distal end configured for generating ionizing species, where the distal end of the source is proximal to the spectrometer entrance, where an atmospheric pressure region is located between the proximal end of the source and the distal end of the source and extends to the proximal end of the spectrometer. The device further comprising a supply adapted to one or more of generate, transfer, conduct and radiate heat and one or more mesh positioned in the atmospheric pressure region, where the analyte is applied on or near the one or more mesh at the proximal end of the source, where the supply can one or more of generate, transfer, conduct and radiate heat to the analyte, where analyte molecules desorbed from the one or more mesh interact with the ionizing species generated by the source to form a plurality of analyte ions which enter the spectrometer.

In various embodiments of the invention, the source operates by a technique selected from the group consisting of electrospray ionization, nano-electrospray ionization, atmospheric pressure matrix-assisted laser desorption ionization, atmospheric pressure chemical ionization, desorption electrospray ionization, atmospheric pressure dielectric barrier discharge ionization, atmospheric pressure low temperature plasma desorption ionization, and electrospray-assisted laser desorption ionization, a direct analysis real time, plasma assisted desorption/ionization, dielectric barrier discharge ionization source, desorption atmospheric pressure chemical ionization, desorption sonic spray ionization, desorption atmospheric pressure photoionization, and flowing atmospheric-pressure afterglow, an atmospheric laser desorption ionization, a Corona discharge, an inductively coupled plasma and a glow discharge source.

In various embodiments of the invention, the spectrometer is selected from the group consisting of a mass spectrometer, a handheld mass spectrometer, an ion mobility spectrometer (IMS) and a handheld IMS. In various embodiments of the invention, the spectrometer is selected from the group consisting of a quadrupole ion trap, a rectilinear ion trap, a cylindrical ion trap, a ion cyclotron resonance trap, an orbitrap, a sector, and a time of flight mass spectrometer.

In an embodiment of the invention, a device for analyzing an analyte comprises a spectrometer configured for analyzing the analyte, with an entrance for accepting analyte ions, a detector for detecting analyzed analyte ions and an atmospheric pressure source configured for generating ionizing species. The device further comprises a flow of the analyte molecules or clusters of analyte and solvent molecules from a solution where the analyte molecules or clusters of analyte and solvent molecules interact with the ionizing species generated by the source to form a plurality of analyte ions which enter the spectrometer and are analyzed. The flow of the analyte molecules or clusters of analyte and solvent molecules can be generated by one or more techniques including matrix assisted laser desorption, secondary ion impact techniques, electrospray, thermospray and electro-hydrodynamic desorption. Prior to forming the flow of analyte molecules or clusters of analyte and solvent molecules, the analyte can be chromatographically separated by interacting with a solid support.

A device for analyzing an analyte comprises an ion mobility spectrometer including an entrance and a detector with a first potential applied to the ion mobility spectrometer entrance, a source configured for generating ionizing species, a supply adapted to one or more of generate heat, transfer heat, conduct heat, radiate heat and apply an electric potential, and two or more mesh positioned between the source and the spectrometer. The analyte is applied on or near a first mesh, where the supply can one or more of generate heat, transfer heat, conduct heat and radiate heat to the analyte to desorb molecules of the analyte, where molecules desorbed from the first mesh interact with the ionizing species generated by the source to form analyte ions. The device where the mesh on which the analyte is applied is grounded. The device where the mesh on which the analyte is applied does not have the first potential. The device where the mesh on which the analyte is applied has a potential that is approximately 100 volts different than the first potential. The device where the mesh on which the analyte is applied has a potential that is approximately 1000 volts different than the first potential. The two or more mesh have two or more potentials, where the two or more potential are approximately 100 volts different than the first potential. The two or more mesh have two or more potentials, where the two or more potential are approximately 1000 volts different than the first potential.

In various embodiments of the invention, the analyte is of at least one state selected from the group consisting of solid phase, liquid phase, and gas phase. In various embodiments of the invention, the analyte is of biological origin. In various embodiments of the invention, the analyte is of non-biological origin. In various embodiments of the invention, the analyte is selected from the group consisting of an industrial work piece, a pharmaceutical product, a pharmaceutical ingredient, a food, a food ingredient, a toxin, a drug, an explosive, a bacterium, and a biological tissue.

While the systems, methods, and devices have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and devices provided herein. Additional advantages and modifications will readily be apparent to those skilled in the art. Therefore, the invention, in its broader aspects, is not limited to the specific details, the representative system, method or device, and illustrative examples shown and described. Accordingly, departures may be made from such details without departing from the spirit or scope of the applicant's general inventive concept. Thus, this application is intended to embrace alterations, modifications, and variations that fall within the scope of the appended claims. Furthermore, the preceding description is not meant to limit the scope of the invention. Rather, the scope of the invention is to be determined by the appended claims and their equivalents.

What is claimed is:

1. A method of analyzing an analyte comprising:
   introducing the analyte onto one or more mesh positioned between a source and an entrance of a spectrometer;
   directing a plurality of ionizing species formed by the source at the one or more mesh;
   heating one or more of the one or more mesh, where analyte molecules desorbed from the one or more mesh interact with the ionizing species to form one or more analyte ions which pass through the entrance of the spectrometer and are analyzed.

2. The method of claim 1, further comprising using a gas ion separator positioned between the one or more mesh and the entrance of spectrometer to improve the efficiency of sampling.

3. The method of claim 1, where the one or more analyte ions are formed at approximately atmospheric pressure.

4. The method of claim 1, where the plurality of ionizing species are formed at approximately atmospheric pressure.

5. The method of claim 1, where the source is selected from the group consisting of a direct analysis real time (DART), Plasma Assisted Desorption/Ionization (PADI), Dielectric Barrier Discharge ionization source (DBDI or DCBI), Desorption Atmospheric Pressure Chemical Ionization (DAPCI), Desorption Sonic Spray Ionization (DeSSI), Desorption Atmospheric Pressure Photoionization (DAPPI), and Flowing Atmospheric-Pressure Afterglow (FAPA) and a desorption electrospray ionization (DESI), an atmospheric laser desorption ionization, a Corona discharge, an inductively coupled plasma (ICP) and a glow discharge source.

6. The method of claim 1, where the heating involves supplying a power to at least one of the one or more mesh of between:
   a lower limit of approximately $10^{-2}$ Watts; and
   an upper limit of approximately $10^3$ Watts.

7. The method of claim 1, where the region between the spectrometer is at approximately atmospheric pressure.

8. The method of claim 1, where a first potential is applied to a first mesh containing the analyte.

9. The method of claim 8, where the first potential is approximately the same potential as a potential applied to the entrance of the spectrometer.

10. The method of claim 1, where a first location on a first mesh is heated independently of a second location on the first mesh.

11. The method of claim 1, where the analyte is delivered as a solution on or near the mesh.

12. A method of analyzing an analyte comprising:
   continuously introducing the analyte onto a mesh positioned between a source and an entrance of a spectrometer;
   directing a plurality of ionizing species formed by the source at the mesh;
   heating the mesh, where analyte molecules desorbed from the mesh interact with the ionizing species to form one or more analyte ions which pass through the entrance of the spectrometer and are analyzed.

13. The method of claim 12, where the one or more analyte ions are formed at approximately atmospheric pressure.

14. The method of claim 12, where the plurality of ionizing species are formed at approximately atmospheric pressure.

15. The method of claim 12, where the source is selected from the group consisting of a direct analysis real time (DART), Plasma Assisted Desorption/Ionization (PADI), Dielectric Barrier Discharge ionization source (DBDI or DCBI), Desorption Atmospheric Pressure Chemical Ionization (DAPCI), Desorption Sonic Spray Ionization (DeSSI), Desorption Atmospheric Pressure Photoionization (DAPPI), and Flowing Atmospheric-Pressure Afterglow (FAPA) and a desorption electrospray ionization (DESI), an atmospheric laser desorption ionization, a Corona discharge, an inductively coupled plasma (ICP) and a glow discharge source.

16. The method of claim 12, where the plurality of ionizing species is formed from a carrier gas.

17. The method of claim 16, where the carrier gas can be heated.

18. A method of analyzing an analyte comprising:
    introducing the analyte onto a first mesh with a first potential applied to the first mesh, where the first mesh is positioned between a source and an entrance of a spectrometer, where the first potential is approximately the same potential as a potential applied to the entrance of the spectrometer, where a second potential is applied to a second mesh, where the second mesh is positioned between the first mesh and the entrance of the spectrometer, where the second potential is different from the first potential;
    directing a plurality of ionizing species formed by the source at the first mesh;
    heating the first mesh, where analyte molecules desorbed from the first mesh interact with the ionizing species to form one or more analyte ions which pass through the entrance for the spectrometer and are analyzed, where the kinetic energy of the analyte ions desorbed from the first mesh can be adjusted by adjusting the second potential.

19. The method of claim 18, where the spectrometer is an ion mobility spectrometer operated at approximately atmospheric pressure.

20. The method of claim 19, where at least one of the first mesh and the second mesh have a potential equal to the potential applied to the ion mobility spectrometer.

* * * * *